United States Patent
Charnegie et al.

(10) Patent No.: US 9,907,530 B2
(45) Date of Patent: Mar. 6, 2018

(54) AUTOMATED CONTROL OF IMAGE EXPOSURE PARAMETERS IN AN INTRA-ORAL X-RAY SYSTEM

(71) Applicant: Dental Imaging Technologies Corporation, Hatfield, PA (US)

(72) Inventors: Jeremy Charnegie, Emmaus, PA (US); Adam T. Palermo, Philadelphia, PA (US)

(73) Assignee: DENTAL IMAGING TECHNOLOGIES CORPORATION, Hatfield, PA (US)

(*) Notice: Subject to any disclaimer, the term of this patent is extended or adjusted under 35 U.S.C. 154(b) by 416 days.

(21) Appl. No.: 14/643,920

(22) Filed: Mar. 10, 2015

(65) Prior Publication Data
US 2016/0262715 A1 Sep. 15, 2016

(51) Int. Cl.
*A61B 6/14* (2006.01)
*A61B 6/00* (2006.01)

(52) U.S. Cl.
CPC .............. *A61B 6/545* (2013.01); *A61B 6/145* (2013.01); *A61B 6/4494* (2013.01); *A61B 6/462* (2013.01); *A61B 6/464* (2013.01); *A61B 6/465* (2013.01); *A61B 6/468* (2013.01); *A61B 6/5294* (2013.01); *A61B 6/54* (2013.01); *A61B 6/542* (2013.01); *A61B 6/547* (2013.01); *A61B 6/4464* (2013.01); *A61B 6/587* (2013.01)

(58) Field of Classification Search
CPC ........... A61B 6/547; A61B 6/542; A61B 6/54; A61B 6/548; A61B 6/545; A61B 6/4233; A61B 6/4241; A61B 6/40; A61B 6/02; A61B 6/14; H04N 5/32
USPC .... 378/97, 108, 109, 110, 111, 112, 147, 38
See application file for complete search history.

(56) References Cited

U.S. PATENT DOCUMENTS

| 7,090,395 B2 | 8/2006 | Glazer |
| 7,599,538 B2 | 10/2009 | Crucs |
| 7,775,713 B2 | 8/2010 | Klemola et al. |
| 9,265,467 B2* | 2/2016 | Kamiya .............. A61B 6/5241 |
| 9,408,581 B2* | 8/2016 | Hyde .................... A61B 6/145 |
| 2012/0093383 A1* | 4/2012 | Claus ................... A61B 6/032 |
| | | 382/131 |
| 2014/0010349 A1 | 1/2014 | De Godzinsky et al. |

FOREIGN PATENT DOCUMENTS

WO 2012/127117 A1 9/2012

* cited by examiner

*Primary Examiner* — Don Wong
(74) *Attorney, Agent, or Firm* — Michael Best & Friedrich LLP

(57) ABSTRACT

Methods and systems for operating x-ray system. One system includes an x-ray source having a plurality of exposure parameters and a controller for the x-ray source. The controller for the x-ray source is configured to receive image characteristic information and automatically adjust the plurality of exposure parameters based on the image characteristic information. The image characteristic information can include an identifier of a predefined sequence of images, an identifier of an image type, a set of values of the plurality of exposure parameters, and a unique identifier of a holder for an x-ray receptor.

33 Claims, 27 Drawing Sheets

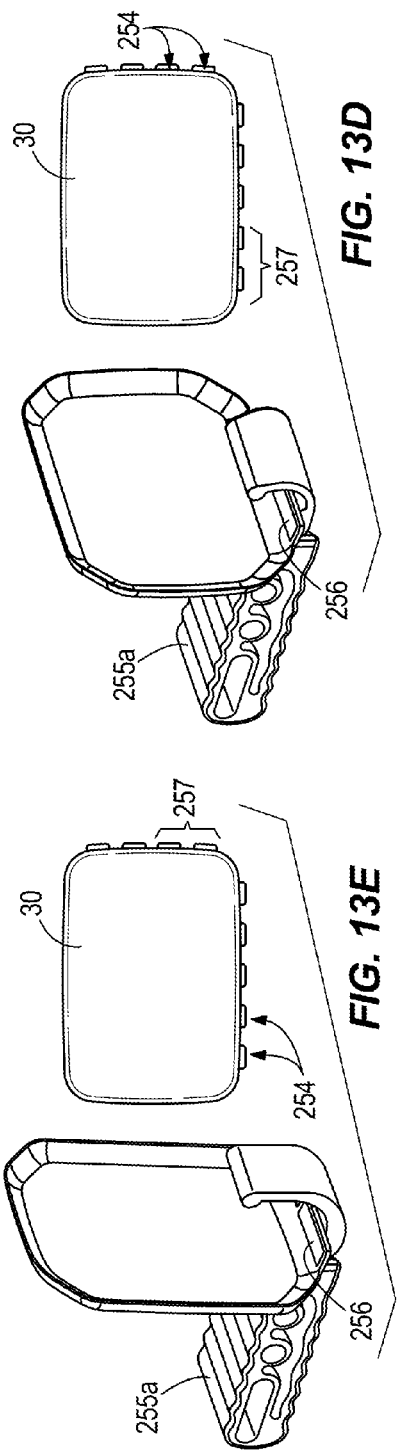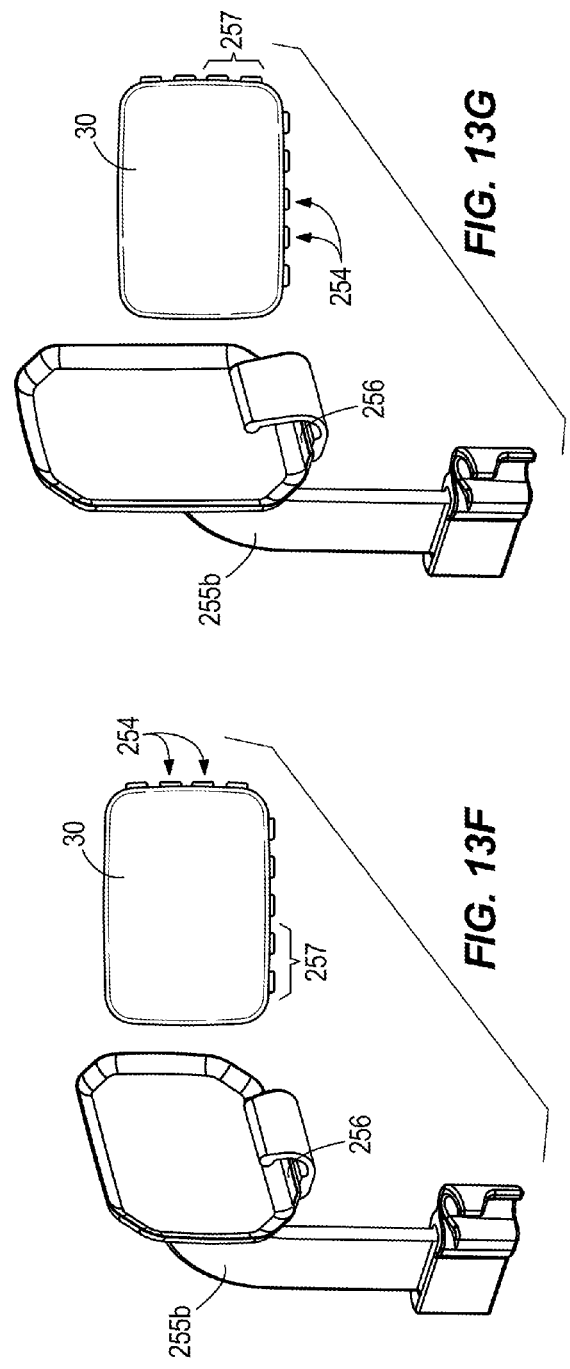

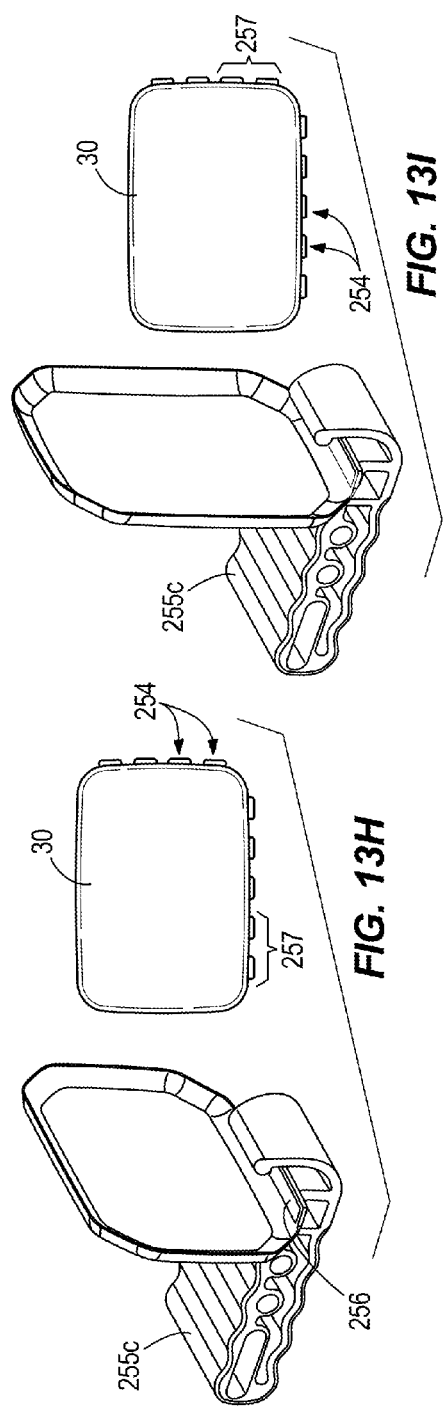
FIG. 13H
FIG. 13I
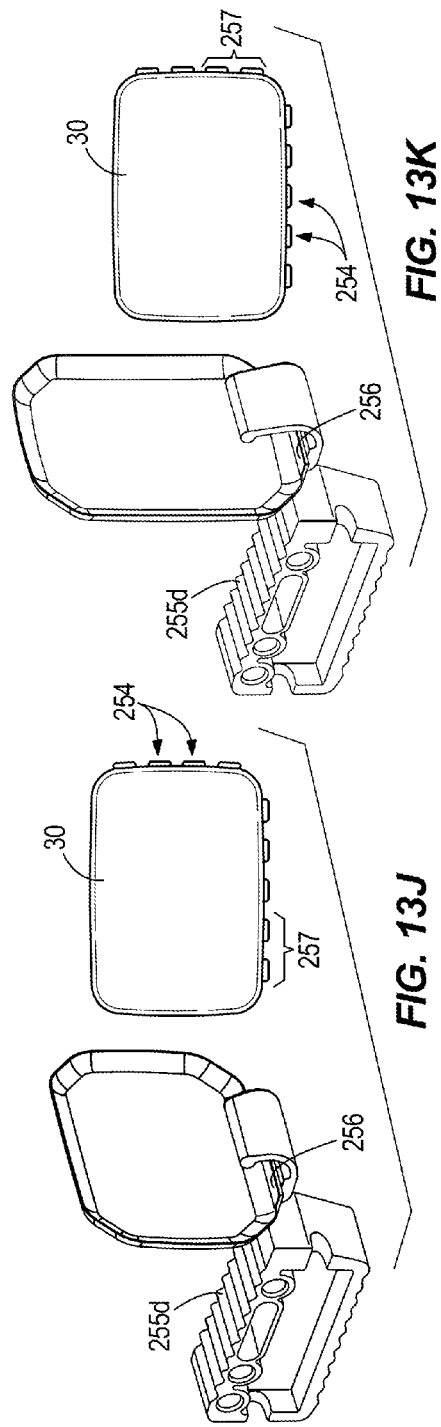
FIG. 13J
FIG. 13K

AUTOMATED CONTROL OF IMAGE EXPOSURE PARAMETERS IN AN INTRA-ORAL X-RAY SYSTEM

FIELD

The present invention relates to intra-oral x-ray systems. More particularly, the invention relates to systems and methods for automatically adjusting exposure parameters for an intra-oral x-ray system.

BACKGROUND

When acquiring intraoral x-ray images, exposure parameters (e.g., voltage, current, and exposure times) can be manually set by an x-ray technician or operator on a user interface that is used to control the x-ray source. Ideally, the exposure parameters should be adjusted based on, among other things, the particular teeth or the particular anatomy being imaged (e.g., anterior teeth, posterior teeth, bitewing (crowns of the posterior teeth), endodontic (tooth pulp), etc.). It is also generally desirable that the exposure parameters be adjusted to minimize x-ray exposure to the patient while still providing a quality image.

SUMMARY

Even though it is generally known that exposure parameters should be adjusted, in practice they are often not. In addition, the parameters are sometimes adjusted incorrectly.

Accordingly, one embodiment of the invention provides a system for automatically controlling or setting exposure parameters for an intra-oral dental x-ray system. Because the parameters ideally vary based on the particular teeth or anatomy being imaged, the system automatically identifies what teeth are being imaged based on at least one of two factors: 1) an assumed predetermined order of image acquisition; and 2) information from receptor holders used when taking the x-ray images.

The receptor holders include different types of holders and each type of holder is designed to hold a sensor or receptor in a position that is suited for a particular type of image acquisition. The holders are designed to provide to an x-ray exposure controller identification information correlated to the type of image being acquired. After receiving the identification information, the controller automatically adjusts the exposure parameters to match the teeth or anatomy associated with the particular holder. Thus, the system automatically adjusts the exposure parameters without requiring input from an x-ray technician or operator.

As is known, a full-mouth series of intra oral x-ray images includes a number of images. In most cases, full-mouth series includes eighteen (18) images or "films": four bitewings, eight posterial periapicals, and six anterior periapicals. The four bitewings typically include two molar bitewings (left and right) and two premolar bitewings (left and right). The eight posterior periapicals typically include two maxillary molar periapicals (left and right), two maxillary premolar periapicals (left and right), two mandibular molar periapicals (left and right), and two mandibular premolar periapicals (left and right). The six anterior periapicals typically include two maxillary canine-lateral incisor periapicals (left and right), two mandibular canine-lateral incisor periapicals (left and right), and two central incisor periapicals (maxillary and mandibular). Certain embodiments of the invention, can adjust the exposure parameters to accommodate differences in each of the images in a full mouth series.

In particular, in one embodiment, the invention provides an x-ray system including an x-ray source and at least one controller. The x-ray source has at least one adjustable exposure parameter, and the at least one controller has memory storing a plurality of image types and a plurality of predetermined settings of the at least one adjustable exposure parameter. The at least one controller is configured to associate each of the plurality of image types with one of the plurality of predetermined settings and automatically select an image type based on image characteristic information. The image characteristic information includes at least one selected from the group consisting of image type information and image sequence information. The at least one controller is further configured to select one of the plurality of predetermined settings based on the selected image type and adjust the at least one exposure parameter based on the selected one of the plurality of predetermined settings.

Another embodiment of the invention also provides an x-ray imaging system including a first controller and a plurality of x-ray receptor holders. Each holder has a particular arrangement of contacts configured to engage contacts of an x-ray receptor, wherein a signal is generated based on the engagement between the contacts of the holder and the contacts of the x-ray receptor. The first controller receives the signal and causes an x-ray source to operate based on the signal.

In addition, another embodiment the invention provides a method of operating an x-ray imaging system that includes an x-ray source and at least one controller. The at least one controller has a memory and the x-ray source has at least one adjustable exposure parameter. The method includes storing, in the memory, a plurality of image types and a plurality of predetermined settings of the at least one adjustable exposure parameter and associating each of the plurality of image types with one of the plurality of predetermined settings. The method also includes automatically selecting, by the controller, an image type based on image characteristic information, the image characteristic information comprising at least one selected from the group consisting of image type information and image sequence information, selecting, by the controller, one of the plurality of predetermined settings based on the selected image type, and adjusting, by the controller, the at least one adjustable exposure parameter based on the selected one of the plurality of predetermined settings.

Yet another embodiment of the invention provides a method of operating an x-ray system that includes an x-ray source and at least one controller. The at least one controller has a memory, and the x-ray source has at least one adjustable exposure parameter. The method includes storing, in the memory, a plurality of image types and a plurality of predetermined settings of the at least one adjustable exposure parameter and associating each of the plurality of image types with one of the plurality of predetermined settings. The method also includes automatically selecting, by the controller, an image type based on image characteristic information, the image characteristic information comprising an identifier of a predefined sequence of images, selecting, by the controller, one of the plurality of predetermined settings based on the selected image type, and adjusting, by the controller, the at least one adjustable exposure parameter based on the selected one of the plurality of predetermined settings.

Other aspects of the invention will become apparent by consideration of the detailed description and accompanying drawings.

BRIEF DESCRIPTION OF THE DRAWINGS

FIGS. 13D-K illustrate various types of receptor holders used in the x-ray system of FIG. 1A or 2 in different orientations and the corresponding engaging contacts of the receptor of FIG. 13A.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
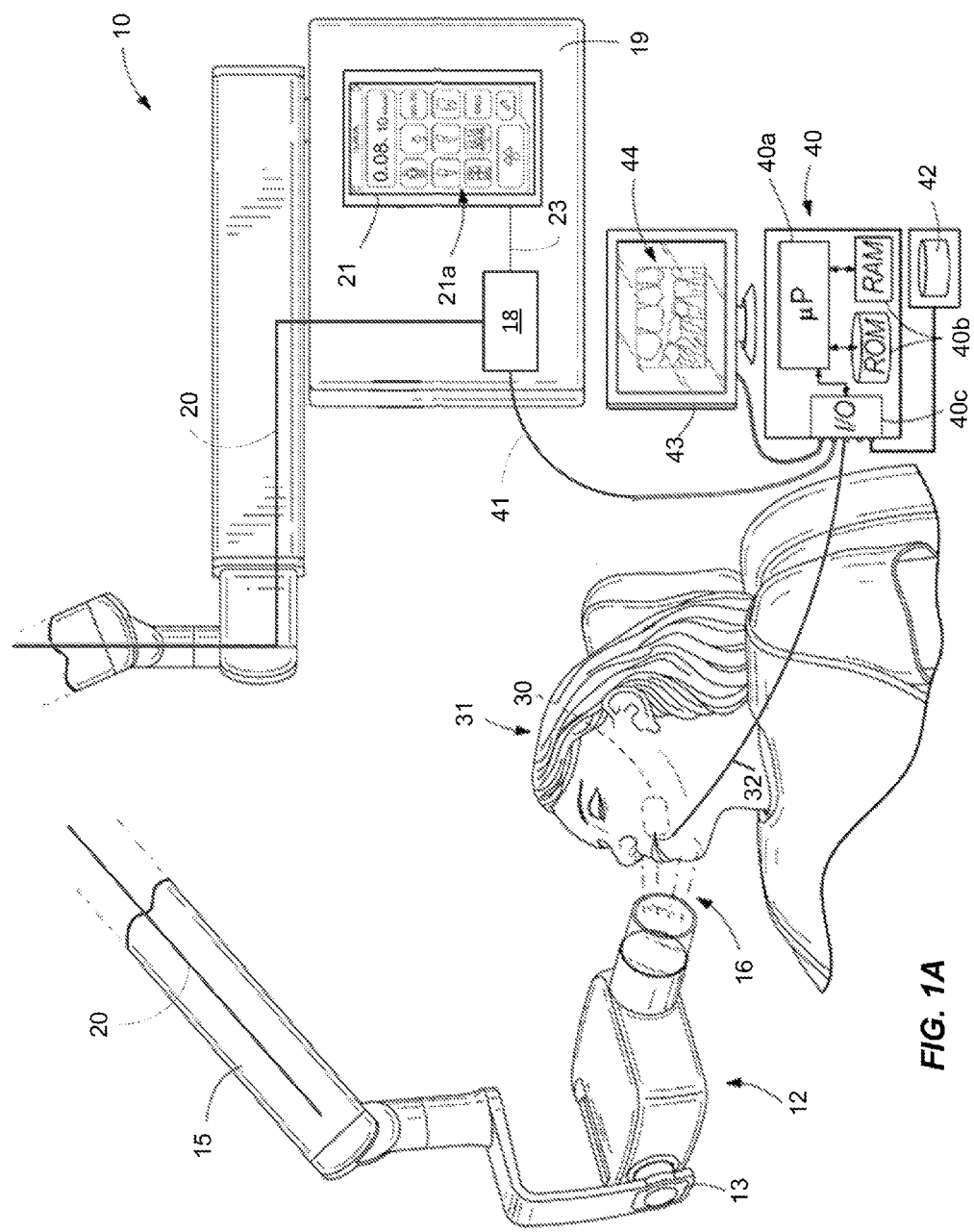
FIGS. 1A and 2 schematically illustrate an intra-oral dental x-ray system.

FIG. 1A illustrates an intraoral dental x-ray system 10. The system 10 includes an x-ray source 12. In the illustrated embodiment, the source 12 is located at an end 13 of a mechanical arm 15. When activated, the x-ray source 12 generates an x-ray stream 16 that has a generally circular cross-section. (Although x-rays are generally invisible, a representation of a stream is illustrated to facilitate understanding of the invention.) In some applications, a collimator (not shown) is used to reduce the size of the stream 16 and generate a smaller x-ray stream having a different shaped cross-section (e.g., rectangular). The collimator can also be used to change the shape of the beam and/or focus the stream on a particular anatomical site of interest. As described below in more detail, the x-ray source 12 includes at least one adjustable exposure parameter.

The system 10 also includes a controller 18. As illustrated in FIG. 1A, the controller 18 can be included inside a housing 19 located at the base or shoulder of the arm 15. In this configuration, the controller 18 is connected to the x-ray source 12 using a connection 20 (e.g., a wire, cable, wireless connection, or the like) that runs from the x-ray source 12 to the controller 18 through the arm 15. It should be understood that although the controller 18 is illustrated as being inside the housing 19 at the base of the mechanical arm 15, in some embodiments the controller 18 is located within the housing of the x-ray source 12.

Figure 1B:
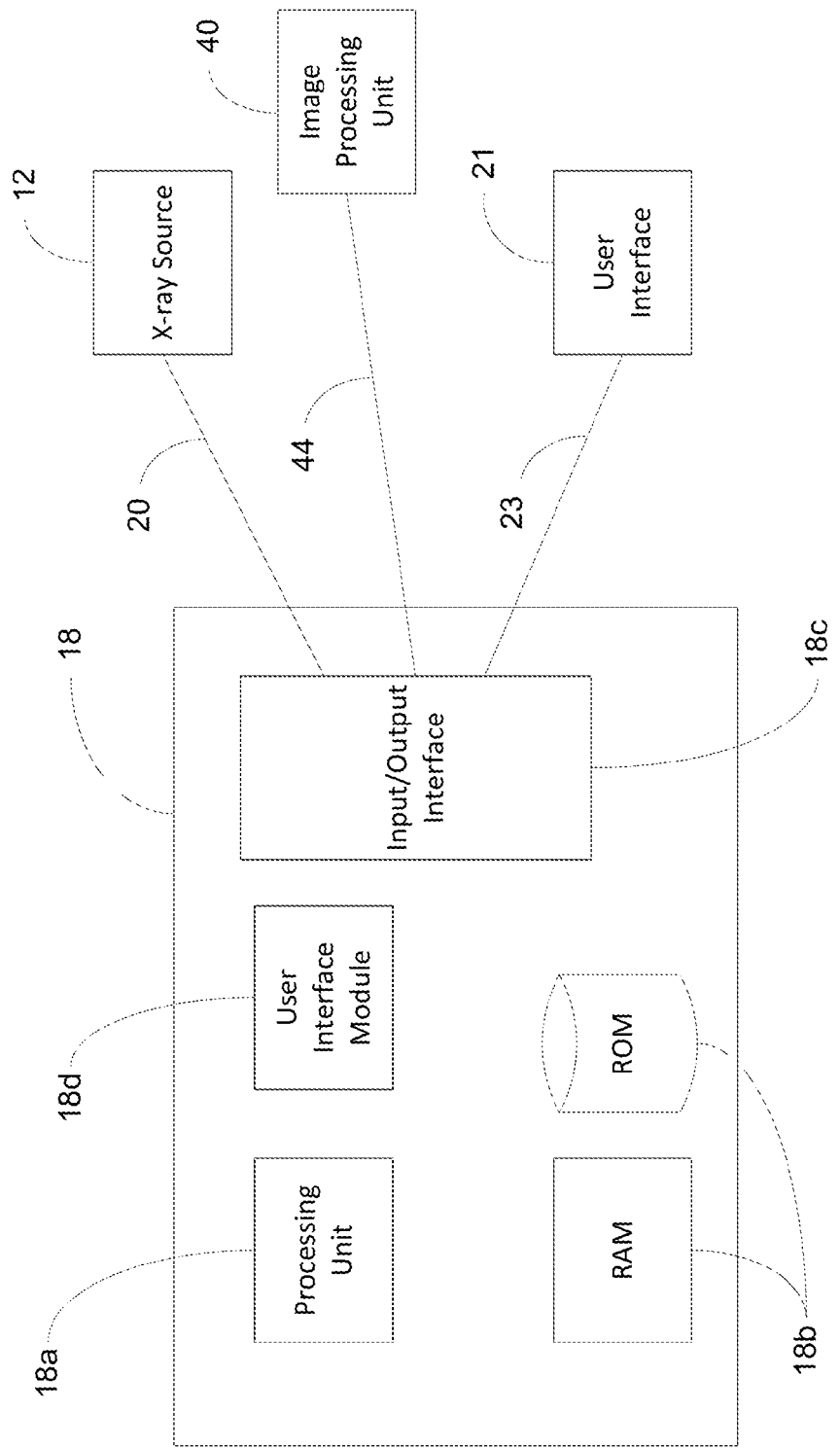
FIG. 1B schematically illustrates a controller included in the x-ray system of FIG. 1A

The controller 18 and the x-ray source 12 are collectively referred to as an x-ray unit. The controller 18 monitors and controls operation of the x-ray source 12. As illustrated in FIG. 1B, the controller 18 includes a processing unit 18a, which can be, for example, a microprocessor or an application-specific integrated circuit ("ASIC"). The controller 18 also includes one or more non-transitory memory modules 18b, for example, a random access memory ("RAM") module and a read-only memory ("ROM") module. The memory modules 18b can store software and/or associated data for monitoring and controlling the x-ray source 12 and/or other aspects of the system 10.

In addition, the controller 18 includes an input/output interface 18c. The input/output interface 18c communicates with systems and devices external to the controller 18, including the x-ray source 12 and a user interface 21. In some embodiments, the controller 18 also includes a user interface module 18d. The user interface module 18d can be configured to communicate with the user interface 21 (e.g., over a universal serial bus ("USB") cable). For example, the user interface module 18d can be configured to generate screens for display on the user interface 21. In addition, the user interface module 18d can be configured to receive inputs from an operator received through the user interface 21. Accordingly, in some embodiments, the user interface module 18d communicates with the user interface 21 rather than the input/output interface 18c.

Figure 2:
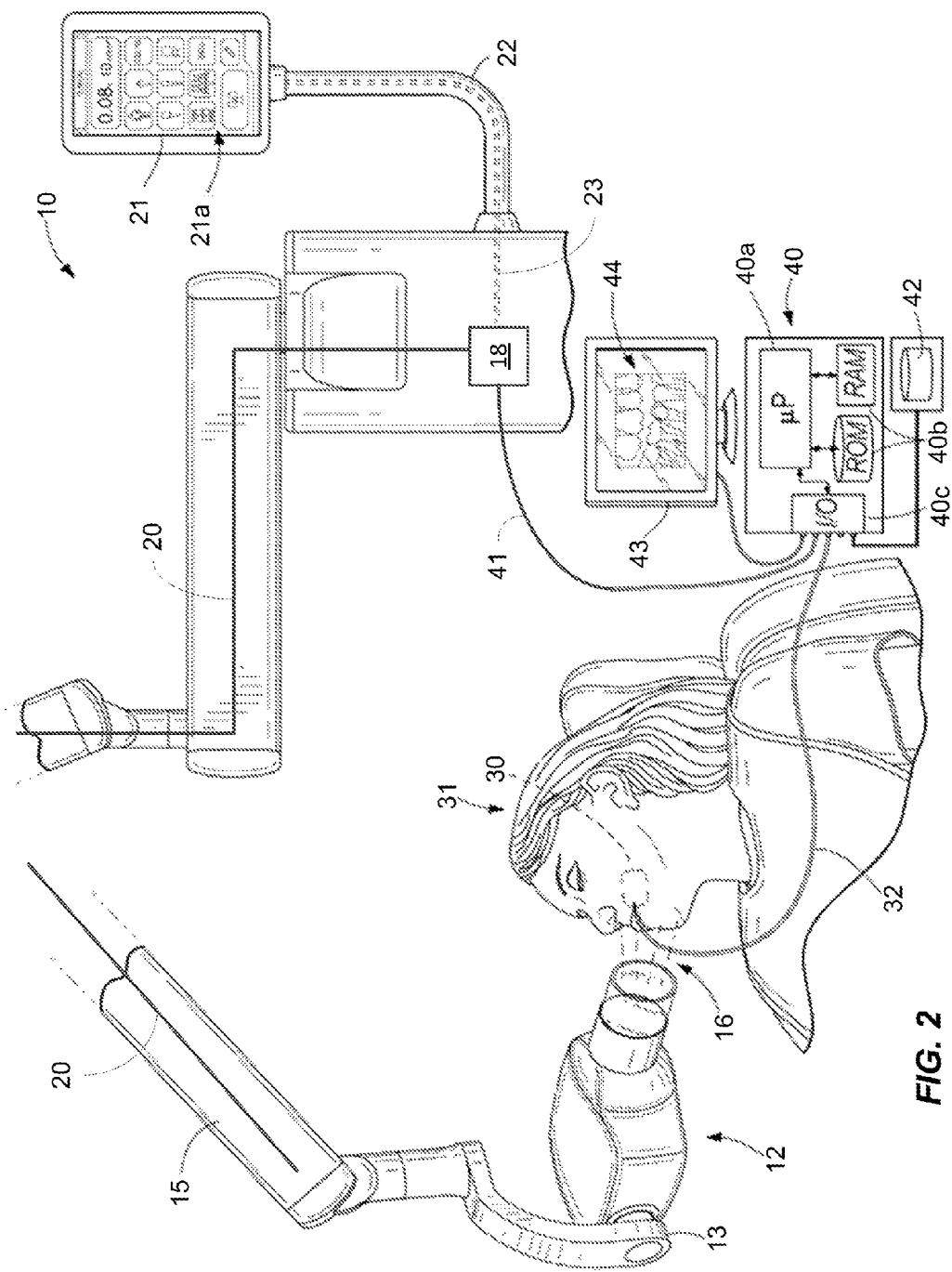

As illustrated in FIGS. 1A and 2, in some embodiments, the user interface 21 includes a touchscreen 21a. However, it should be understood that the user interface 21 can include different types of input and output devices and combinations of the same (e.g., a keyboard, tactile buttons, a joystick, a mouse, a non-touch screen display, etc.). The user interface 21 is located external to x-ray source 12 and the controller 18. In some embodiments, the user interface 21 is contained within the housing 19 located at the base or shoulder of the arm 15 (see FIG. 1A). In other embodiments, the user interface 21 can be mounted on a separate extension 22 connected to the arm 15 (see FIG. 2). In some embodiments, the extension 22 is flexible to allow an operator to change the position of the user interface 21. It should be understood that the user interface 21 can also be located outside of the room where the x-ray source is located to allow the operator to avoid radiation exposure. In other embodiments, the user interface 21 can be located in the same room as the x-ray source but protected from radiation exposure using shielding material.

Regardless of where the user interface 21 is positioned, the user interface 21 is connected to the controller 18 (i.e., through the input/output interface 18c) over a connection 23. In some embodiments, the connection 23 (e.g., a wire or cable) between the controller 18 and the user interface 21 can be positioned external to the arm 15. However, in other embodiments, the connection 23 can be accomplished by routing a wire from the controller 18 to the user interface 21 internal to the housing 19. Also, in some embodiments, the user interface 21 can communicate with the controller 18 using a wireless connection, a wired connection, or a combination of wired and wireless connections. An operator can use the user interface 21 to manually control the x-ray source 12. In particular, an operator can use the user interface 21 to manually set one or more adjustable exposure parameters of the x-ray source 12. The exposure parameters can include a voltage (e.g., in kilovolts ("kV")), a current (e.g., in milliamps ("mA")), and an exposure time (e.g., in milliseconds ("ms")). The controller 18 receives the parameters and uses the parameters (in combination with the software and data stored in the memory modules 18b) to monitor and control the x-ray source 12.

In some embodiments, the x-ray source 12 is activated in response to a signal received from a remote switch (not shown). The remote switch communicates with the controller 18, which, in turn, starts and/or stops the x-ray stream 16. The remote switch can communicate with the controller 18 over a wired or wireless connection (e.g., through the input/output interface 18c). An operator can start and stop the x-ray source 12 using the remote switch from a different room or location than the x-ray source 12 to avoid radiation exposure.

As shown in FIGS. 1A and 2, the x-ray source 12 is positioned (e.g., manually by an operator (not shown)) so that the x-ray stream 16 is directed toward an intra-oral x-ray sensor or receptor 30 located in the mouth of a patient 31. The receptor 30 can include a digital detector, a sensor, a film plate, or an imaging plate (e.g., phosphorescent plate or other type of imaging plate). As described in more detail below, the receptor 30 is positioned within a holder prior to being inserted in the patient's mouth. The holder helps properly position the receptor 30 for imaging particular teeth or anatomy. Different holders are used depending on what teeth or region of the patient's mouth are being imaged. In the examples illustrated in FIGS. 1A and 2, a wire, cable, or similar connection 32 connects the receptor 30 to an image processing unit 40. The connection 32 between the receptor 30 and the image processing unit 40 can alternatively be a wireless connection, a fiber-optic connection, or other connection suitable for transmitting data between the devices. In some embodiments, the connection 32 also provides an electrical return path that allows electrical signals to be provided to and/or received from the receptor 30 and or a holder for the receptor 30. The electrical signals can be used to identify a type or placement of the receptor 30 that indicates what image in a sequence of images is being acquired. In other embodiments, a separate connection (e.g., a separate wire) is used to provide the electrical signals.

The image processing unit 40 includes a processing unit 40a, which can be, for example, a microprocessor or an ASIC. The image processing unit 40 also includes one or more non-transitory memory modules 40b, e.g., a RAM module and a ROM module. The memory modules 40b can store software and data for processing image data collected by the receptor 30 (e.g., to generate an image). The memory modules 40b can also store image data and/or associated metadata for the image data (e.g., a log of exposure times, etc.). In addition, as described in more detail below, the memory modules 40b can store software and data for automatically controlling exposure parameters. In some embodiments, the software stored on the memory modules 40b is the Dexis Imaging Suite provided by Dental Imaging Technology Corp.

As illustrated in FIGS. 1A and 2, the image processing unit 40 also includes an input/output interface 40c. The input/output interface 40c communicates with systems and devices external to the image processing unit 40, including, for example, the receptor 30 and the controller 18. For example, the image processing unit 40 can communicate with the controller 18 over a connection 41. The connection 41 can include a wire or a cable. In other embodiments, the connection 41 can include a wireless connection. Although the connection 41 illustrated in FIGS. 1A and 2 is shown as being external to the housing 19, it should be understood that the connection 41 can be routed through one or more components of the system 10 (e.g., the housing 19, the arm 15, etc.).

In some embodiments, the input/output interface 40c also communicates with one or more an external data storage devices 42 that store images acquired using the system 10. As also illustrated in FIGS. 1 and 2, the input/output interface 40c can also communicate with one or more display devices 43. The display device(s) 43 can be used to display images acquired through use of the system 10. In particular, during operation of the system 10, image data is captured by the receptor 30, the data is processed by the image processing unit 40, and the processed data is sent to a display device 43 where it can be viewed as an image 44. (Image 44 is drawn more distinctly than an x-ray image would typically appear.) In some embodiments, the display device(s) 43 include a touchscreen that receives input from an operator. The image processing unit 40 can also include one or more additional peripheral devices for receiving input from an operator (e.g., a keyboard, mouse, joystick, etc.).

It should be understood that the receptor 30 could be configured to carry out all or a portion of the image processing carried out by the image processing unit 40. In other words, imaging processing could be distributed between the receptor 30 and the unit 40. For example, processing hardware could be located in the body of the receptor 30 or in the connection 32 connecting the receptor 30 to the image processing unit 40.

As noted above, an operator can use the user interface 21 to set one or more adjustable exposure parameters for the x-ray source 12. To minimize radiation exposure to the patient and improve image quality, the exposure parameters should be varied based on the particular teeth being imaged. However, in many cases, operators do not adjust the parameters for different teeth images. Rather, operators typically set the exposure parameters once and use the same parameters for all images acquired for the patient. In addition, even if an operator adjusts the parameters for the particular image being acquired, the operator may incorrectly adjust the parameters or may not adjust the parameters to optimal values. Accordingly, it would be advantageous for the system 10 to be configured to automatically adjust the exposure parameters for the particular type of image being acquired.

Figure 3:
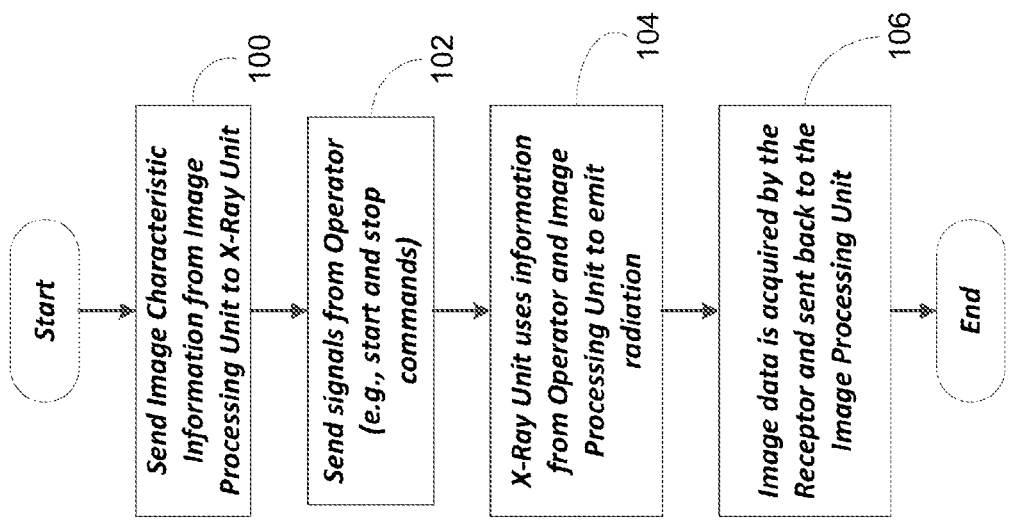
FIG. 3 is a flow chart illustrating a method of automatically adjusting exposure parameters using an image processing unit included in the x-ray system of FIGS. 1A or 2.

For example, FIG. 3 is a flow chart illustrating one method for automatically adjusting the exposure parameters. As illustrated in FIGS. 1A, 1B, and 2, the image processing unit 40 communicates with the x-ray unit (e.g., the controller 18, which communicates with the x-ray source 12). Accordingly, the image processing unit 40 can send image characteristic information to the x-ray unit (at 100). As described in more detail below, the image characteristic information can include one or more values for adjustable exposure parameters (e.g., voltage, current, and exposure time), image type information (e.g., an image type identifier), or image sequence information (e.g., a sequence or series identifier). The controller 18 uses the image characteristic information to automatically adjust the exposure parameters for a particular image. As illustrated in FIG. 3, the operator can also provide commands or data to the x-ray unit (at 102). For example, the operator can provide commands to the x-ray unit through the user interface 21. The operator can also issue start and/or stop commands to the x-ray unit through a remote switch as described above.

The controller 18 operates the x-ray source 12 (at 104) according to the image characteristic information and any additional commands or data received from the operator. The receptor 30 captures image data based on the x-ray stream 16 generated by the x-ray source 12, and the image data is transmitted to the image processing unit 40 for processing and display (at 106).

Figure 4:
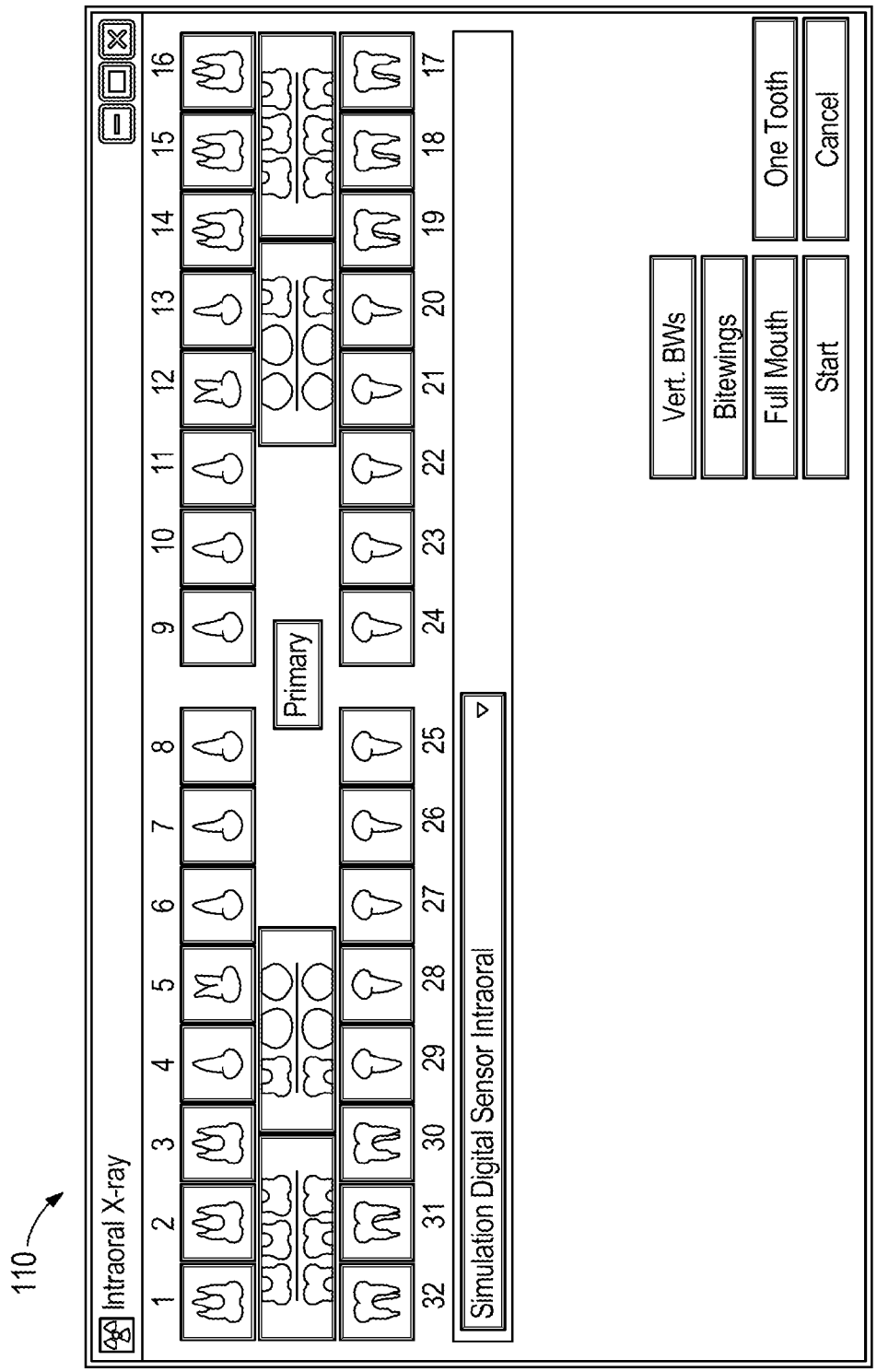
FIG. 4 is a screen illustrating a sequence of images included in a full mouth series.
Figure 5A:
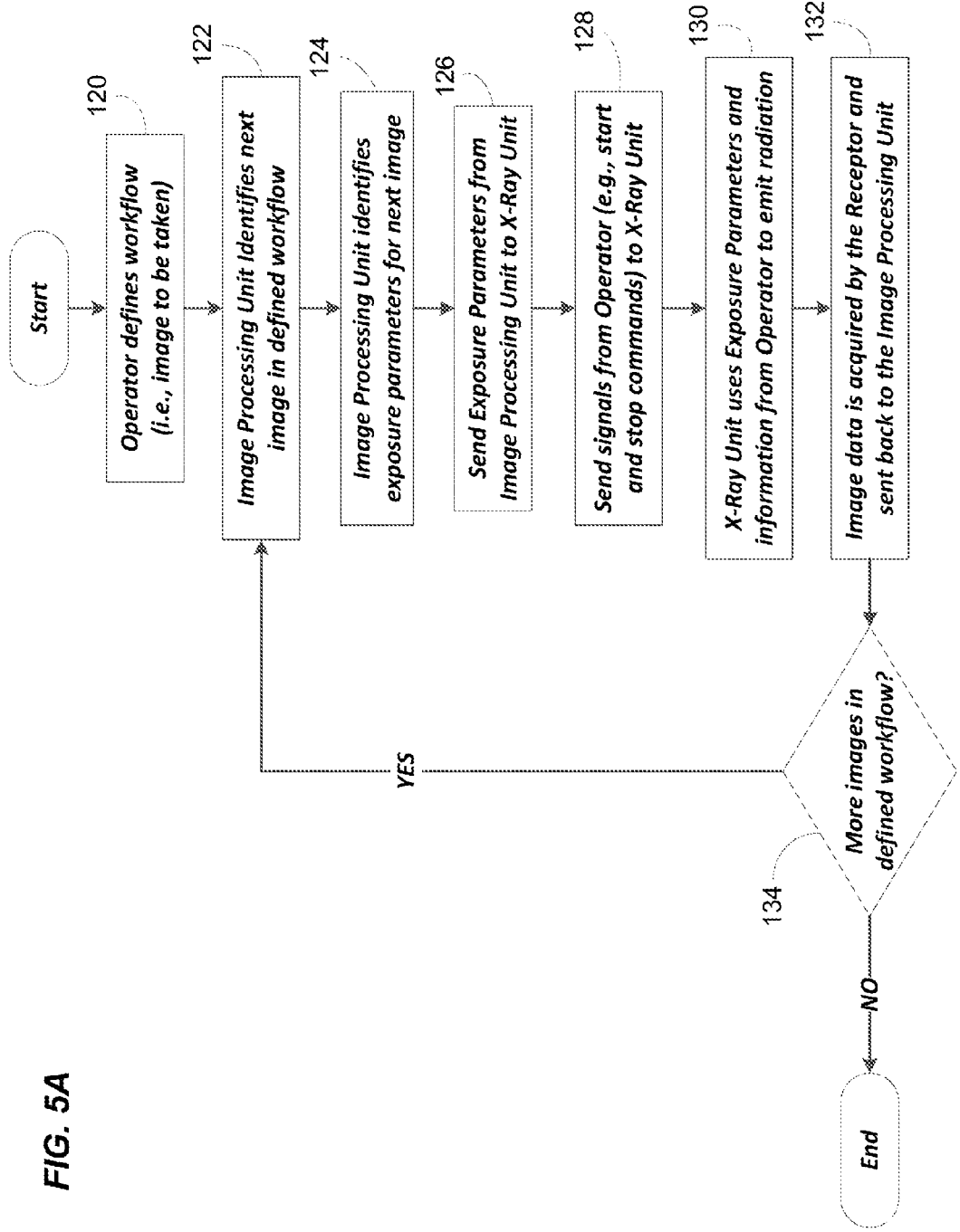
FIG. 5A is a flow chart illustrating a method of automatically adjusting exposure parameters for a sequence of images using an image processing unit included in the x-ray system of FIG. 1A or 2.

As noted above, the image characteristic information can include exposure parameters, an image sequence or series identifier, or an image type identifier. For example, in some embodiments, the image processing unit 40 is configured to perform particular series or sequences of image acquisitions. When the system 10 is used to perform a full mouth series, image data is captured by the receptor 30 according to a predefined sequence. For example, FIG. 4 illustrates a screen shot displayed by the image processing unit 40 illustrating a sequence of images obtained as part of a full mouth series (sometimes referred to as a "tooth map"). In some embodiments, as the images are acquired for a full mouth series, the tooth map 110 is updated to highlight the next image to be acquired. As noted, it is common for eighteen images to be obtained for a full mouth series, but more or fewer images may be obtained depending on the particular imaging sequence that is desired Accordingly, the image processing unit 40 can use a predefined sequence of image to identify the next image acquired by the system 10 and, consequently, the exposure parameters for such an image, which the unit 40 transmits to the controller 18 as the image characteristic information. For example, FIG. 5A illustrates a method for setting exposure parameters for a sequence of images. As illustrated in FIG. 5A, after a user defines the workflow (i.e., the image(s) to be taken in a predefined sequence) through the image processing unit 40 (at 120), the image processing unit 40 identifies the next image (i.e., the first image) in the predefined sequence associated with the defined workflow (at 122). The image processing unit 40 then identifies the exposure parameters for the next image (at 124). To identify exposure parameters associated with a particular image in a predefined sequence of image acquisitions, the image processing unit 40 (or an external data storage device 42) can store one or more data or look-up tables that map exposure parameters to particular image acquisitions. For example, without limitation, the memory modules 40b or an external data storage device 42 accessible by the image processing unit 40 can store a plurality of image types and a plurality of predetermined settings of at least one adjustable exposure parameter associated with the x-ray source 12. The image processing unit 40 can also associate each of the plurality of image types with one of the plurality of predetermined settings to form a data table. One sample data table is provided below. However, it should be understood that different data tables can be used for different types of patients (e.g., child versus adult), different types of imaging equipment or media (e.g., different receptors, different film speeds, etc.), different portions of anatomy being imaged, etc. For example, without limitation, typical voltage settings can range from about 60 kV to about 70 kV, typical current settings can range from about 4 mA to about 7 mA, and typical exposure times can range from about 0.2 seconds to about 1.0 seconds, but other values can also be used in accordance with embodiments of the present invention. In addition, in some cases (as illustrated in Table 1 below, for example) the voltage and current will be same for different types of images, whereas in other cases the voltage and current values may vary. Also, in some embodiments, the same exposure parameters can be associated with a sub-set of the images acquired as part of a full mouth scan. In particular, each image acquired as part of a full mouth series may not be associated with different exposure parameters.

TABLE 1

| Image Identifier | Voltage (kV) | Current (mA) | Exposure Time (ms) |
|---|---|---|---|
| Bitewing | 65 | 6 | 0.400 |
| Molar | 65 | 6 | 0.400 |
| Incisor | 65 | 6 | 0.250 |
| Bicuspid | 65 | 6 | 0.320 |
| Occlusal | 65 | 6 | 0.630 |

Accordingly, upon receiving the image characteristic information, the image processing unit 40 selects an image type (e.g., an image identifier) and accesses a data table associated with the selected image type. The image processing unit 40 uses the accessed data table to select one or more predetermined settings (i.e., values for one or more adjustable exposure parameters for the x-ray source 12). As described below, the image processing unit 40 transmits the predetermined settings to the controller 18, which uses the settings to automatically adjust one or more exposure parameters of the x-ray source. As mentioned above, in some embodiments, for a series or sequence of images, different sub-sets of the sequence of images can be associated with different settings. For example, the image processing unit 40 can be configured to use a data table to select a first set of values for the exposure parameters for a first sub-set of images included in a sequence of images and a second set of values for the exposure parameters for a second sub-set of images included in the sequence of images.

The image processing unit 40 can also be configured to measure the exposure level (signal level) of one or more previously-taken or acquired images to adjust the stored exposure parameters. For example, the image processing unit can compare a measured exposure level of a previous image to a preset optimum value (or an optimum range or window). If the observed exposure level is higher than optimum, this can indicate that the patient has received an unnecessarily high dose of x-rays, and if the observed exposure level is too low, the image quality may be sub-optimal. Once the difference from the optimum exposure value (or range) is determined, the image processing unit 40 corrects the lookup table exposure factors for the next image in the sequence with a level shift based on the difference. This adjustment can, for example, have the effect of automatically accounting for differences in patient size based on acquired images.

After the unit 40 identifies the exposure parameters associated with the next image (i.e., the first image) (at 124), the unit 40 transmits the identified exposure parameters to the controller 18 prior to the acquisition of the next image (at 126). The controller 18 uses the received exposure parameters and any information received from the operator (e.g., through the user interface 21) (at 128) to control the x-ray source 12 to emit radiation (at 130). Image data for the image is then acquired by the receptor 30 and sent back to the image processing unit 40 (at 132).

After receiving the image data for the first image, the image processing unit 40 determines if the user-defined workflow includes additional images (at 134). As noted above, a user-defined workflow can be associated with a predetermined order accessible by the image processing unit 40. Accordingly, the image processing unit 40 can determine whether additional images need to be taken by considering the predetermined order. Alternatively, if an operator prefers a different order than the predefined order for a particular series, the operator can designate the next image prior to each x-ray exposure (e.g., using a tooth map 110 as illustrated in FIG. 4, which can be displayed on a display device 43).

If the workflow includes additional images, the image processing unit 40 identifies the next image in the predefined sequence (e.g., based on the predetermined order or an operator designation) (at 122) and repeats the exposure parameter determination process as described above and sends the exposure parameter settings to the controller 18 prior to the next image acquisition. Alternatively, if the image processing unit 40 determines that the workflow does not include any additional images (i.e., the final image of the sequence has been acquired), the exposure parameter setting process ends.

In some embodiments, in addition to or as an alternative to including the exposure parameters, the image characteristic information includes an identifier of a particular image or a particular sequence of images. For example, as described above, an operator can select a particular predefined sequence of images or can select a custom sequence of images (e.g., by selecting individual images for acquisition). Accordingly, the image processing unit 40 can send an image identifier or an image sequence identifier to the controller 18, and the controller 18 can use the identifier to determine the exposure parameters for the next image acquisition, e.g., by using data table(s) as described above. For example, in some embodiments, the controller 18 stores the data table(s) described above (e.g., in one of the memory modules 18*b*) and uses the data tables directly to determine exposure parameters. Accordingly, it should be understood that the functionality of the image processing unit 40 can be distributed between the controller 18 and the unit 40 in various combinations.

Figure 5B:
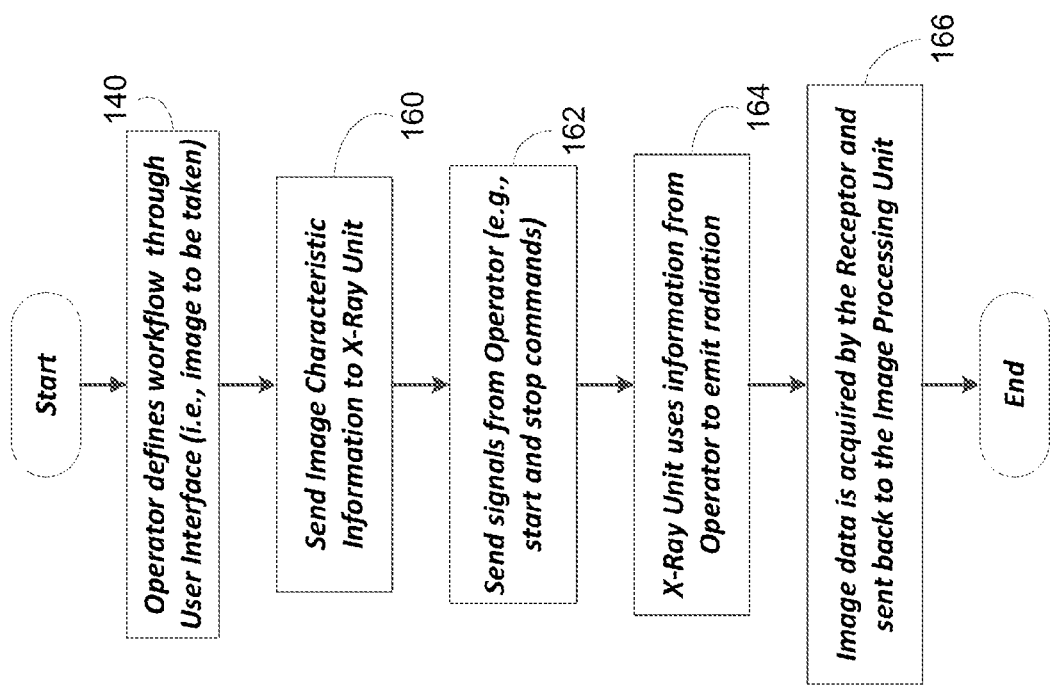
FIG. 5B is a flow chart illustrating an alternative method of automatically adjusting exposure parameters using an x-ray source controller included in the x-ray system of FIG. 1A or 2.
Figure 5C:
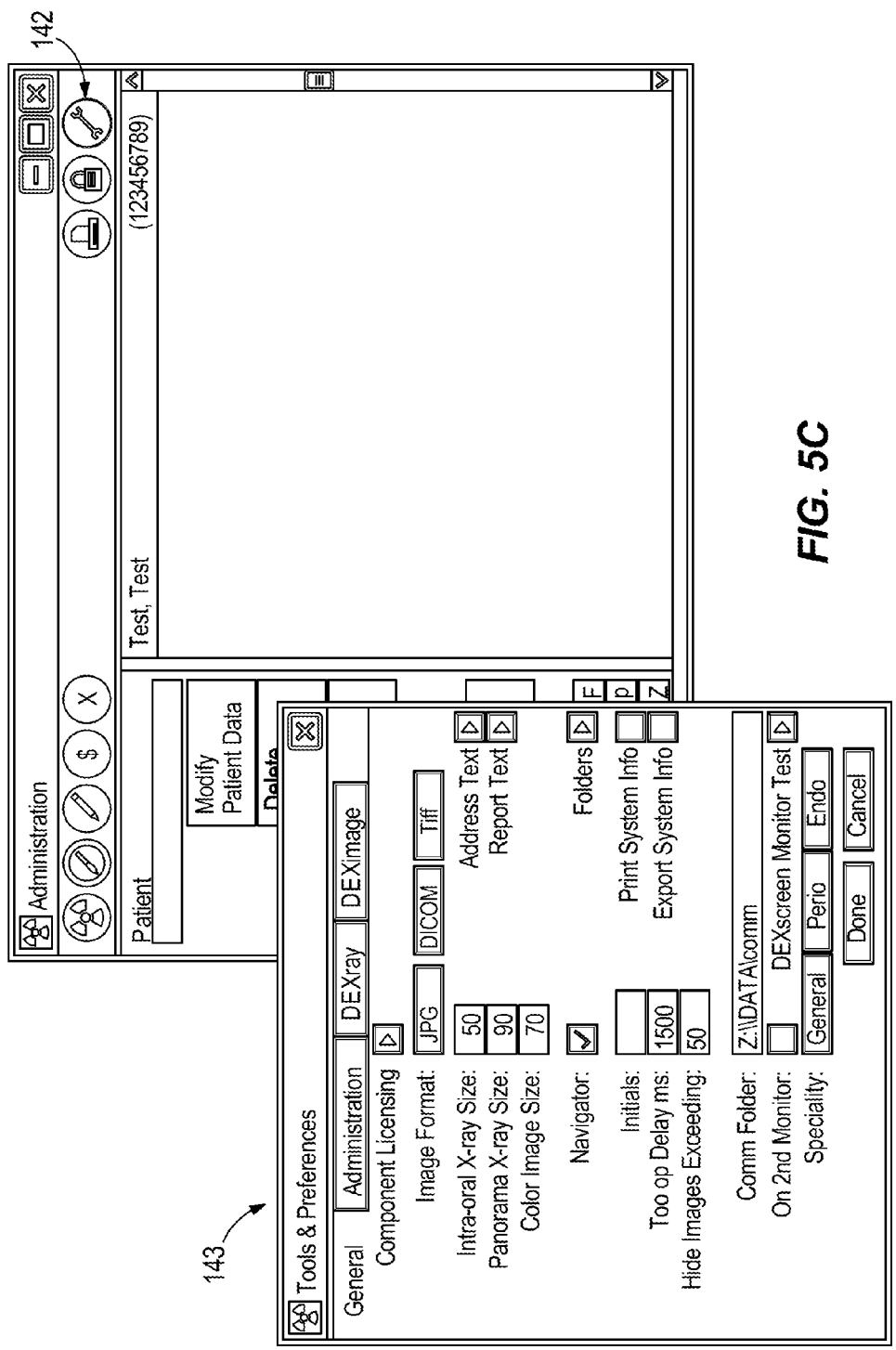
FIGS. 5C-F illustrate a user interface for creating a customized scan sequence.
Figure 5D:
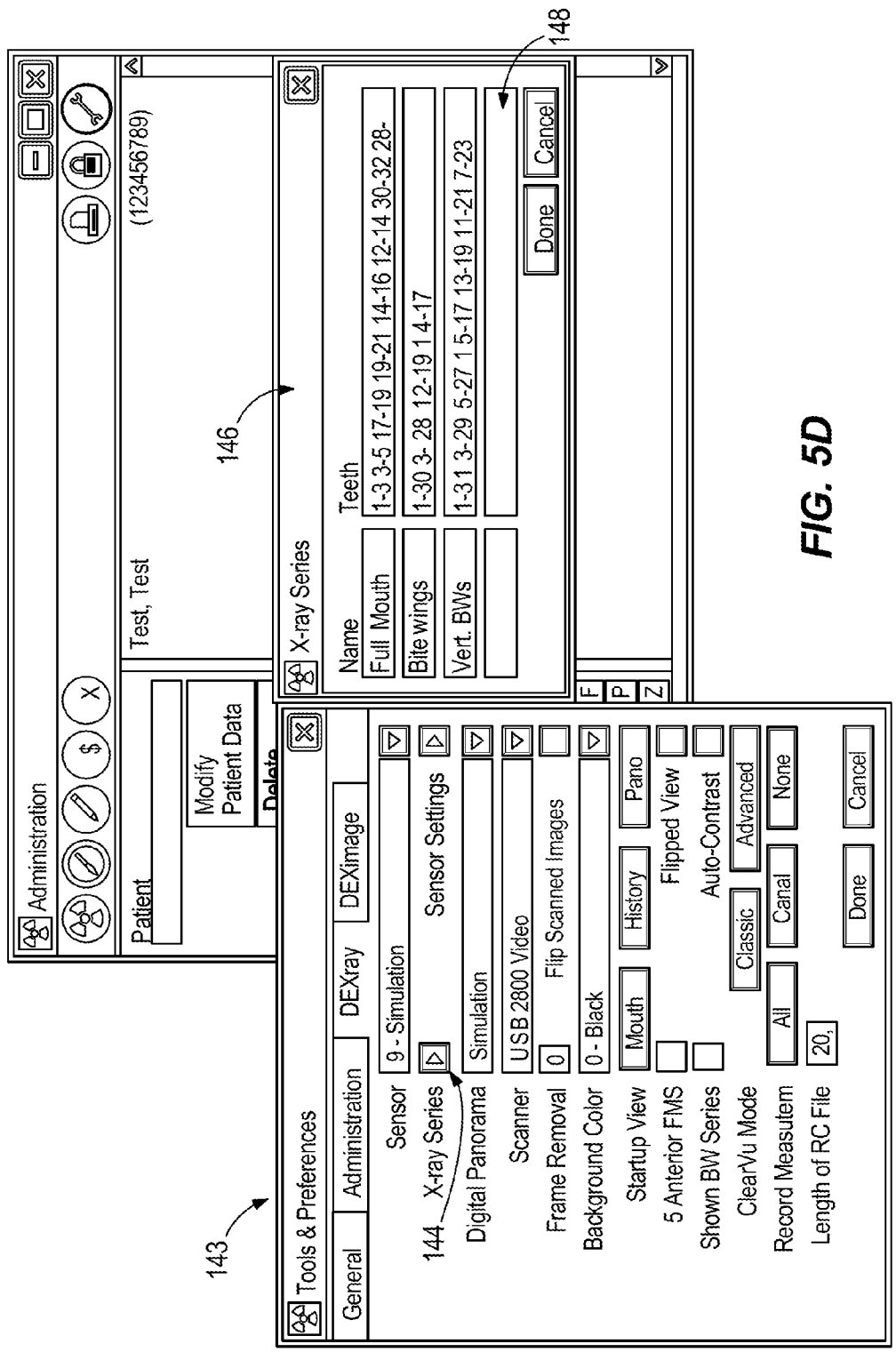
Figure 5E:
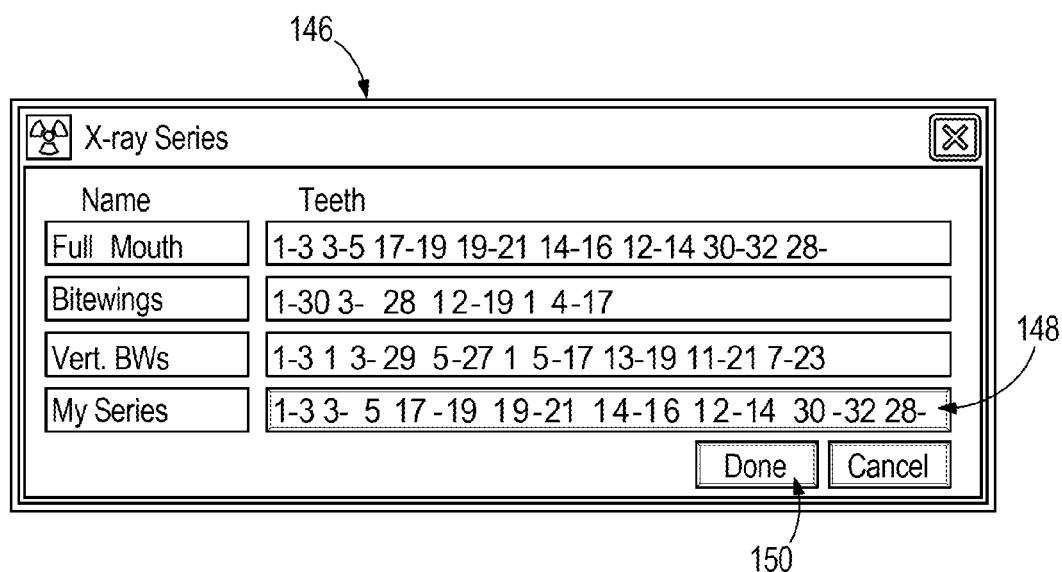
Figure 5F:
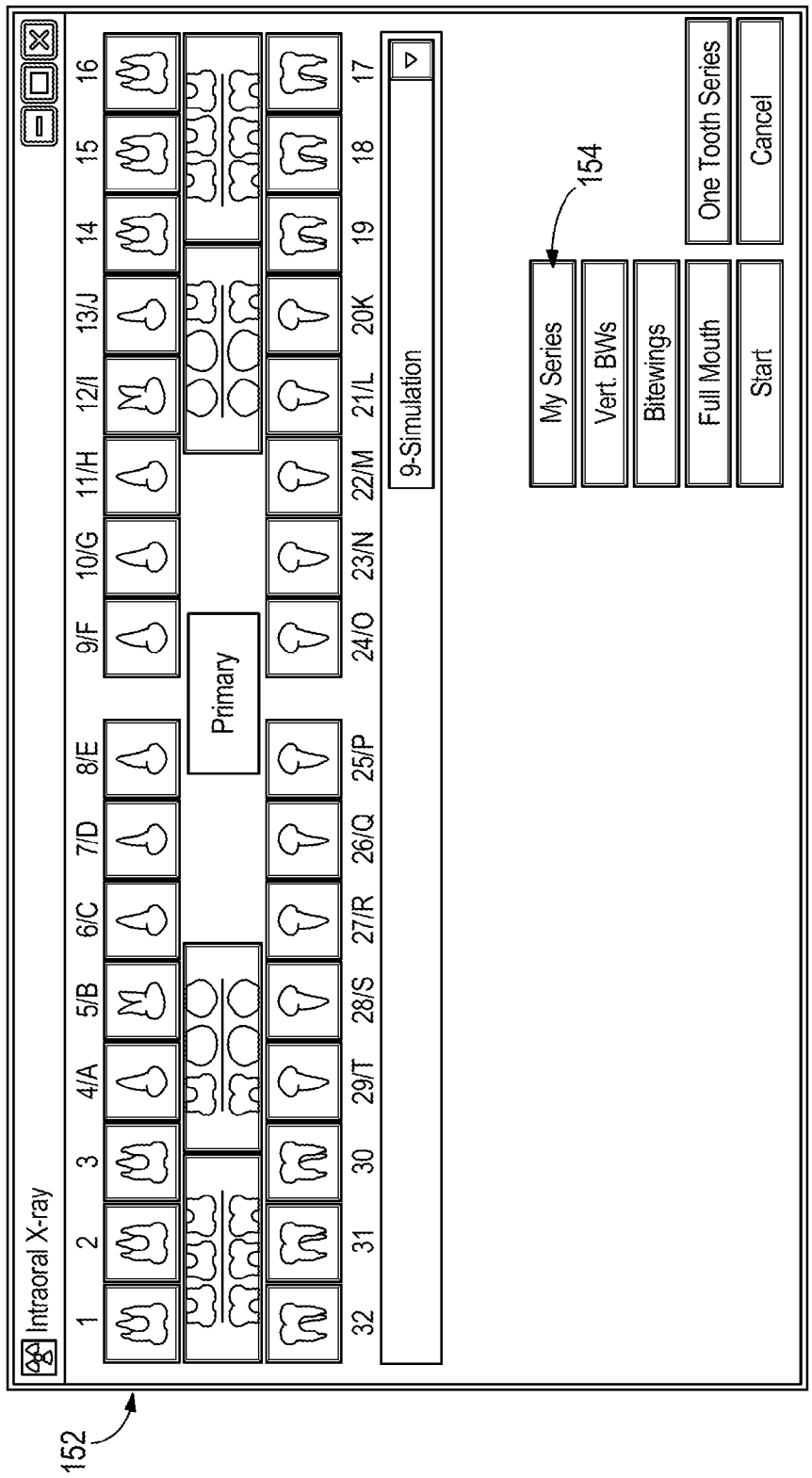

Also, in some embodiments, the x-ray unit (i.e., the controller 18) is configured to receive image characteristic information from sources other than the image processing unit 40. For example, as illustrated in FIG. 5B, an operator can initiate a predefined scan sequence or specify a customized scan sequence using the user interface 21 (at 140). For example, as illustrated in FIG. 5C, to create a customized scan sequence, an operator can select an icon 142 on the user interface 21 to access tools and preferences for the system 10. The user interface 21 can then display a "Preferences" tab 143 (see FIGS. 5C and 5D). From the "Preferences" tab, an operator can select an "x-ray series" button (e.g., an arrow) 144. Selecting this icon causes the user interface 21 to display an "x-ray series" window 146. As illustrated in FIG. 5E, using an empty field 148 within the window 146, an operator can enter a custom series name and custom tooth numbers (e.g., with a space between each number). When finished, the operator can select a "done" button 150. Therefore, when an operator uses the user interface 21 to operate the system 10, a tooth map window 152 displayed on the user interface 21 includes the newly-created custom series (see button 154 in FIG. 5F).

Accordingly, returning to FIG. 5B, the controller 18 receives the operator selections as the image characteristic information from the user interface 21 and uses the image characteristic information to identify the exposure parameters for each image in the sequence (e.g., using the data table(s) described above) (at 160). The controller 18 then applies the identified parameters as it controls the x-ray source 12 (at 162), which may also be based on other commands or data received from the operator, such as a start or stop command from a remote switch (at 164). The receptor 30 acquires image data as the x-ray source 12 emits radiation and sends the acquired image data to the image processing unit 40 for further processing and storage (at 166).

Alternatively or in addition, the image processing unit 40 can be configured to automatically identify a particular image being acquired based on the holder used for the receptor 30. For example, as described above, different holders are used to acquire different images (e.g., bitewing, posterior, anterior, endodontic, etc.). Accordingly, because the image processing unit 40 is connected to the receptor 30, the receptor 30 can be configured to identify the type of holder being used and forward this information to the image processing unit 40. The image processing unit can use the information from the receptor 30 to identify the type of image being acquired, and can provide image characteristic information to the x-ray unit based on the identified image type.

Figure 6:
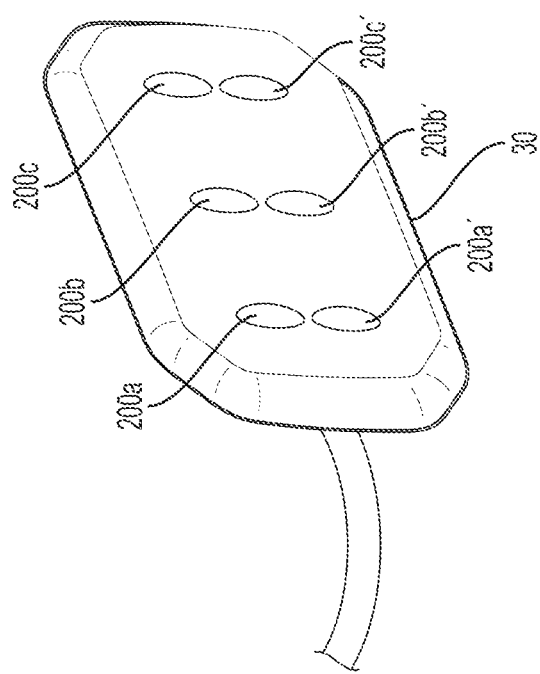
FIG. 6 illustrates a receptor used in the x-ray system of FIG. 1A or 2.
Figure 7:
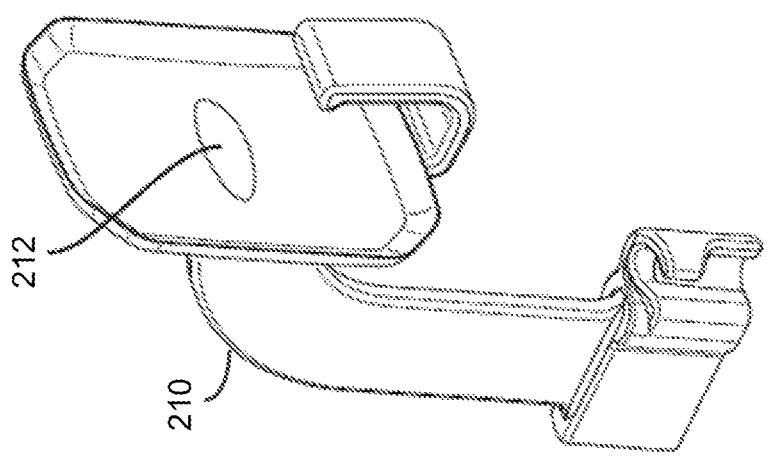
FIG. 7 illustrates a holder for the receptor of FIG. 6.
Figure 8:
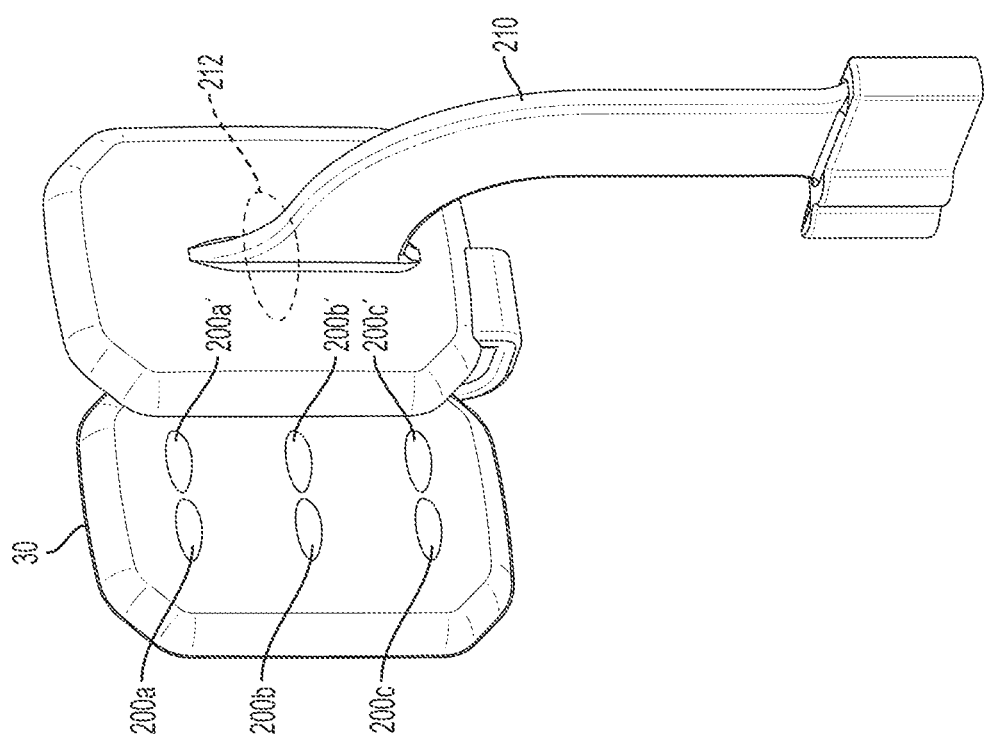
FIGS. 8-12 illustrate different receptor holders used in the x-ray system of FIG. 1A or 2.

For example, FIG. 6 illustrates a receptor 30. The receptor 30 includes a plurality of electrical pins or contacts 200. In some embodiments, the receptor 30 includes three pairs of contacts 200*a* and 200*a*', 200*b* and 200*b*', and 200*c* and 200*c*'. However, it should be understood that fewer or more contacts can also be used (e.g., to account for a smaller or larger number of different holders), and the contacts 200 can be arranged in different arrangements than as illustrated in FIG. 6. During use, the receptor 30 is placed within a holder. The holder also includes one or more electrical contacts that align with one or more of the contacts 200. The contact in the holder creates an electrical path between at least one of the pairs of contacts in the receptor 30 to complete an electrical circuit. Accordingly, using the electrical signal provided through the completed electrical circuit, the number and arrangement of the contacts of the holder that align with and engage with contacts 200 of the receptor 30 can be identified and used by receptor 30, and ultimately, the image processing unit 40, to identify the image being acquired. For example, FIG. 7 illustrates a bitewing holder 210. The bitewing holder 210 includes a single electrical contact 212. As illustrated in FIG. 8, the contact 212 of the holder 210 aligns with middle contacts 200*b* and 200*b*' of the receptor 30. Therefore, when the receptor 30 detects an electrical connection at the middle contacts 200*b* and 200*b*' but not the other pairs of contacts 200*a* and 200*a*' and 200*c* and 200*c*', the unit 40 identifies that a bitewing holder 210 is being used, and, consequently, a bitewing image is being taken. After identifying that a bitewing image is being taken, the image processing unit 40 can use a data table as described above to identify the exposure settings relating to a bitewing image.

Figure 9:
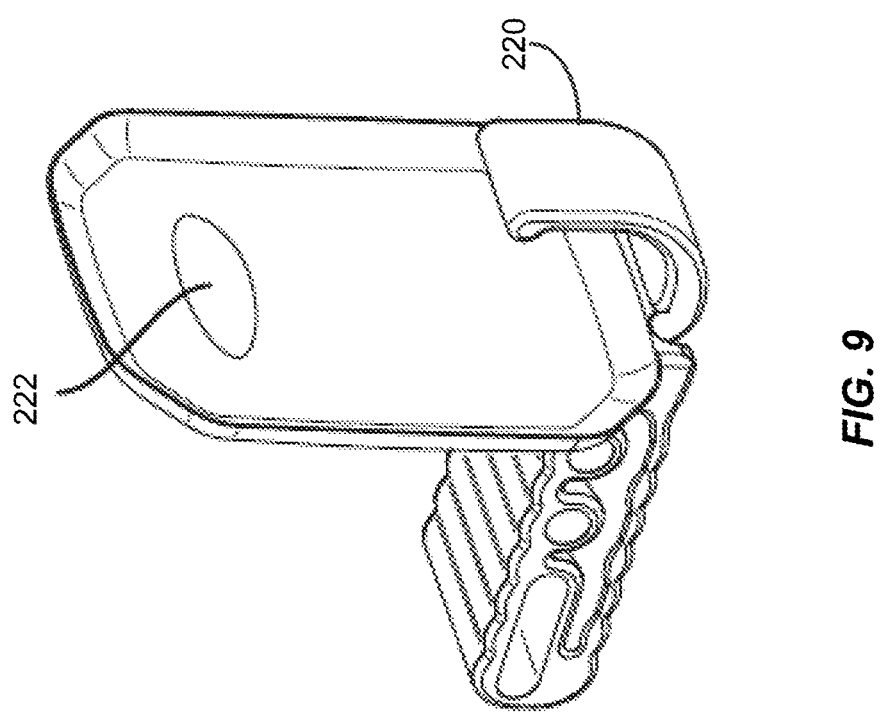

Similarly, as illustrated in FIG. 9, an anterior holder 220 includes a single electrical contact 222 that aligns with the contacts 200c and 200c' of the receptor 30. Therefore, when the receptor 30 detects an electrical connection at the contacts 200c and 200c' but not at the other pairs of contacts 200a and 200a' and 200b and 200b', the unit 40 identifies that an anterior holder 220 is being used, and, consequently, an anterior image is being taken.

Figure 10:
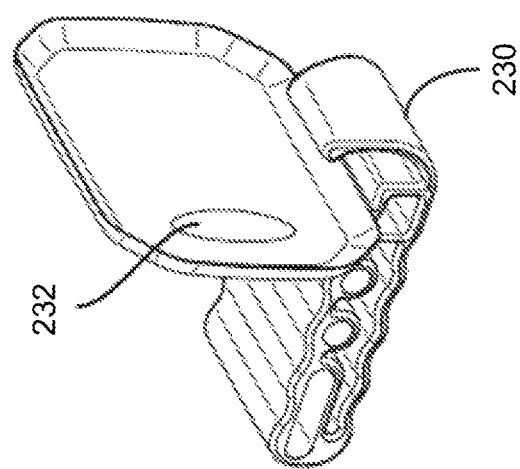

FIG. 10 illustrates a posterior holder 230. The posterior holder 230 includes a single electrical contact 232 that aligns with the contact 200a and 200a' of the receptor 30. Accordingly, when the receptor 30 detects an electrical connection at the contacts 200a and 200a' but not at the other pairs of contacts 200b and 200b' and 200c and 200c', the image processing unit 40 identifies that a posterior holder 230 is being used and, consequently, a posterior image is being taken.

Figure 11:
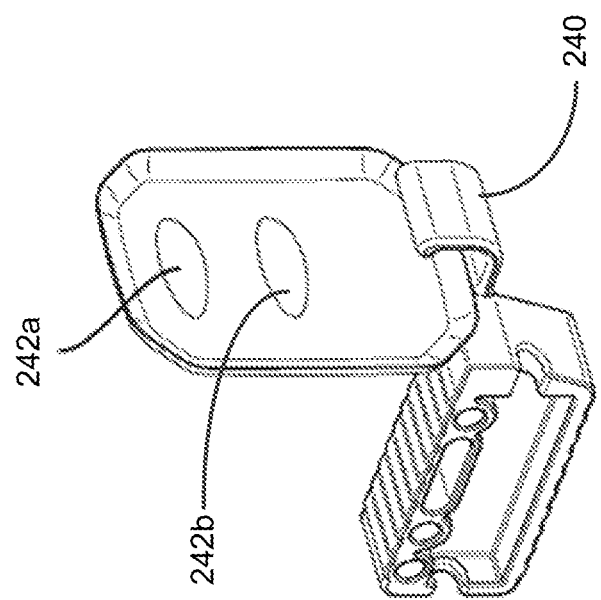
Figure 12:
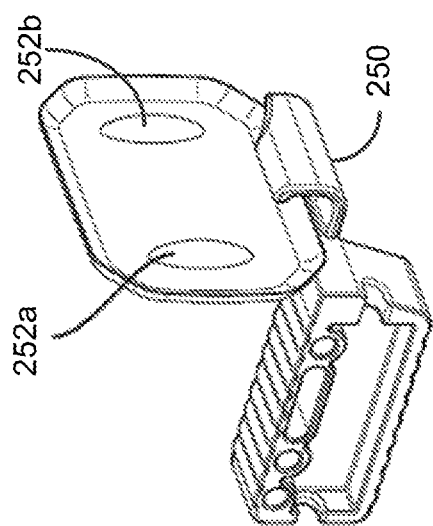

FIG. 11 illustrates an endodontic vertical holder 240. The endodontic vertical holder 240 includes two contacts 242a and 242b that align with the contacts 200b and 200b' and 200c and 200c' of the receptor 30. Accordingly, when the receptor 30 detects an electrical connection at the contacts 200b and 200b' and 200c and 200c' but not at contact 200a, the image processing unit 40 identifies that an endodontic vertical holder 240 is being used and, consequently, an endodontic image is being taken. Similarly, FIG. 12 illustrates an endodontic horizontal holder 250. The endodontic horizontal holder 250 includes two contacts 252a and 252b that align with the contacts 200a and 200a' and 200c and 200c' of the receptor 30. Accordingly, when the receptor 30 detects an electrical connection at the contacts 200a and 200a' and 200c and 200c' but not at contact 200b and 200b', the image processing unit 40 identifies that an endodontic horizontal holder 250 is being used and, consequently, an endodontic image is being taken.

Figure 13A:
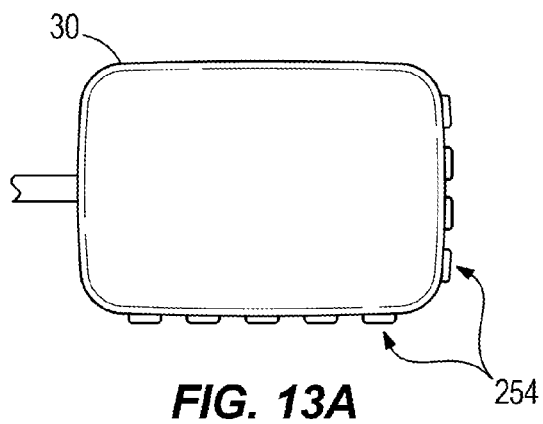
FIG. 13A is a top view of a receptor used in the x-ray system of FIG. 1A or 2, the receptor including a series of contacts on an outer edge.
Figure 13B:
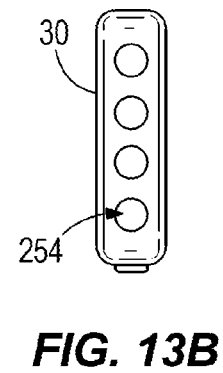
FIG. 13B is a side view of the receptor of FIG. 13A.
Figure 13C:
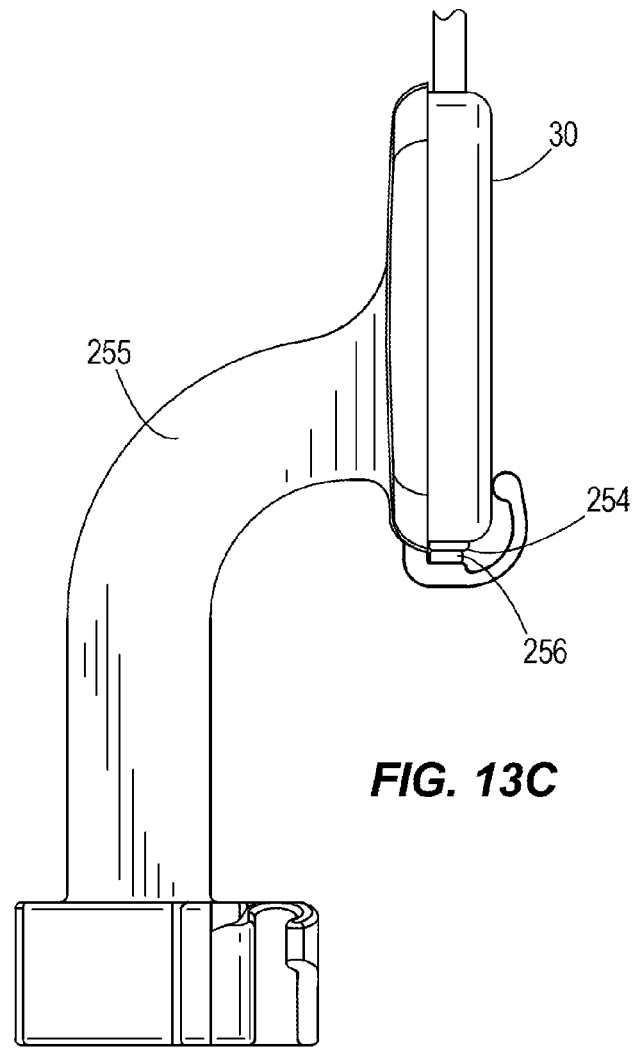
FIG. 13C is a side of the receptor of FIG. 13A mating with a receptor holder used in the x-ray system of FIG. 1A or 2.

It should be understood that the contacts illustrated in FIGS. 6-12 can be positioned at different locations on the receptor 30 and/or the holder and the position and orientation of the contacts illustrated in these figures is provided as one illustrative example. For example, in some embodiments, a series of contacts 254 can be placed on the outer edge(s) of a receptor 30 (see FIGS. 13A and 13B), and the corresponding holder 255 can have a contact strip 256 that will engage unique combinations of contacts 254 on the receptor 30 (see FIG. 13C). Accordingly, in this embodiment, the contacts 254 on each receptor 30 can be the same but different contacts 254 contact the contact strip 256 depending on the orientation or position of the receptor 30 and/or the holder 255 when the receptor 30 is mated with the holder 255 (and/or the type of holder 255 used with the receptor 30).

For example, FIGS. 13D and 13E illustrate two different orientations of a holder 255a (i.e., orientated as a posterior holder in FIG. 13D and orientated as an anterior holder in FIG. 13E). In each orientation, FIGS. 13D and 13E illustrate the particular contacts 254 of the receptor 30 that engage with the contact strip 256 on the holder 255a (engaging contacts are labeled as 257). Accordingly, because different contacts 254 engage with the contact strip 256 in each orientation, the type of image being taken can be identified based on the engaging contacts 257. Similarly, FIGS. 13F and 13G illustrate two different orientations of a bitewing holder 255b (i.e., orientated as a vertical bitewing holder in FIG. 13F and orientated as a horizontal bitewing holder in FIG. 13G). In each orientation, different contacts 254 of the receptor 30 engage with the contact strip 256 on the holder 255b (engaging contacts are labeled as 257). Likewise, FIGS. 13H and 13I illustrate two different orientations of an endodontic UL-LR holder 255c (i.e., a horizontal orientation in FIG. 13H and a vertical orientation in FIG. 13I) and the corresponding engaging contacts 257, and FIGS. 13J and 13K illustrate two different orientations of an endodontic LL-LR holder 255d (i.e., a horizontal orientation in FIG. 13J and a vertical orientation in FIG. 13K) and the corresponding engaging contacts 257.

Figure 14A:
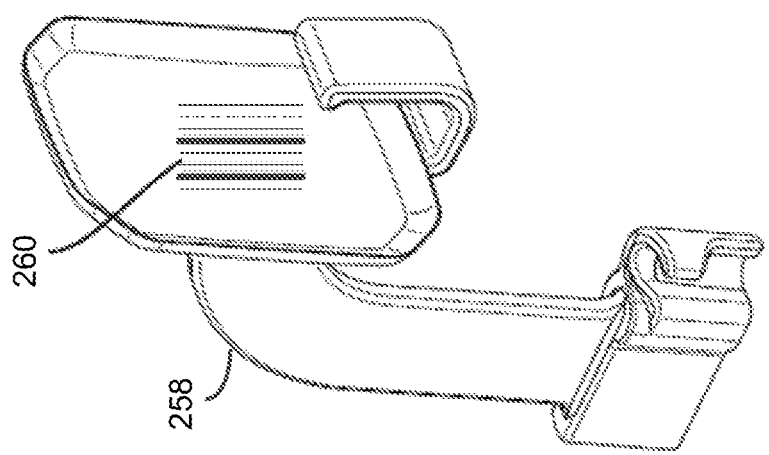
FIG. 14A illustrates a receptor holder used in the x-ray system of FIG. 1A or 2, the receptor including an optical or magnetic pattern.
Figure 14B:
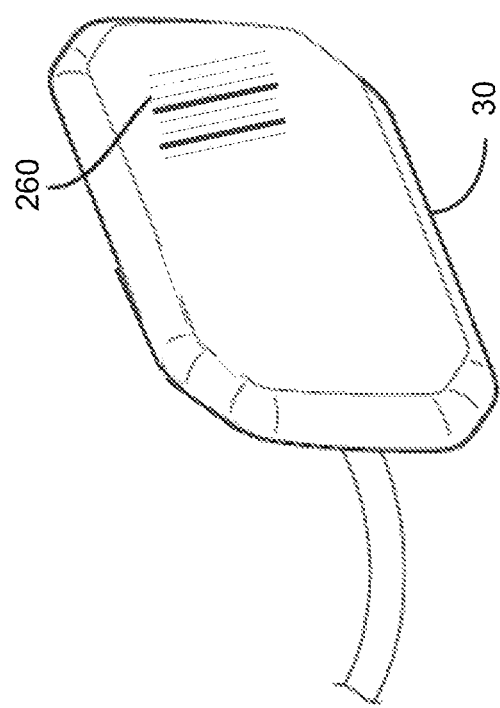
FIG. 14B illustrates a receptor used in the x-ray system of FIG. 1A or 2, the receptor including an optical or magnetic pattern.

It is to be understood that although the examples above use various patterns of electrical contacts to indicate the image type, the invention is not limited to the use of electrical contacts. Alternatively, or in addition, other kinds of indicator elements can be used. For example, as illustrated in FIG. 14A, a receptor holder 258 can contain a pattern 260, including for example an optical pattern (e.g., a 1D or 2D bar code), an arrangement of magnets, or patterned magnetic material, and the receptor 30 can include one or more detectors (e.g., optimal and/or magnetic sensors) to detect the pattern 260. In addition or alternatively, the pattern 260 can be disposed on the receptor 30 (see FIG. 14B), and the receptor holder 258 can include sensors (e.g., electrical, optical, and/or magnetic sensors) to detect the pattern 260. Optionally, the sensors on the receptor holder 258 can be arranged in a pattern indicating the kind of receptor holder.

A receptor 30 or receptor holder in accordance with the invention can also include one or more gravity sensors to indicate the orientation of the receptor 30 and holder with respect to the earth. This can be helpful, for example, to indicate whether the patient 31 is sitting upright, reclining, or lying down, which can resolve ambiguity as to which part of the mouth is being imaged if that is not apparent solely from the relative orientation of the sensor and the holder. The gravity sensors can comprise, for example, one or more 3-axis sensors.

Figure 15A:
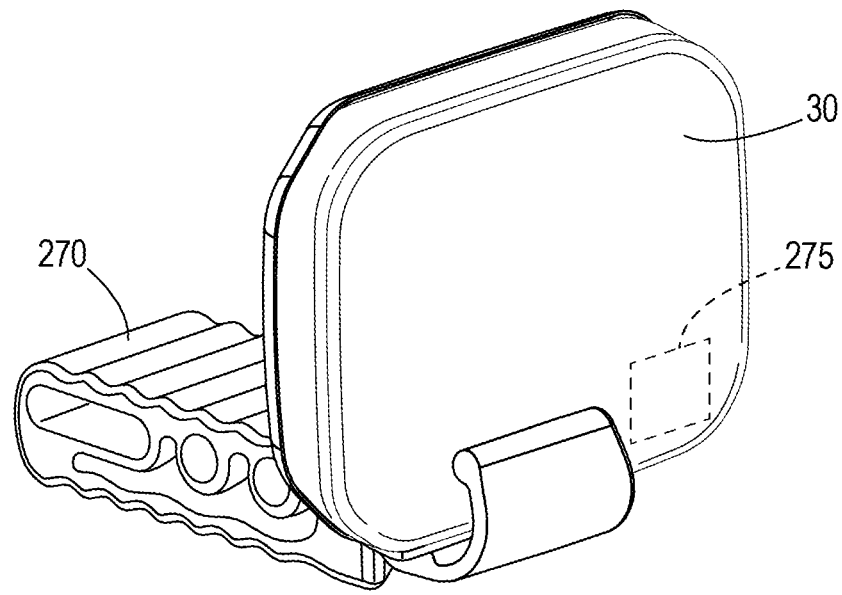
FIGS. 15A and B illustrate a holder and a receptor holder used in the x-ray system of FIG. 1A or 2, the receptor including a gravity sensor.
Figure 15B:
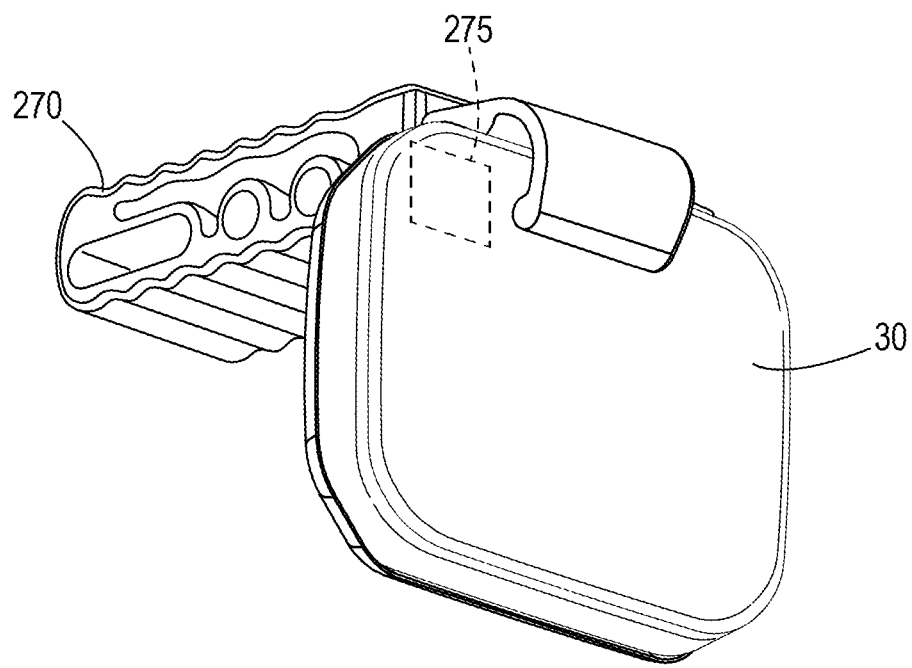

For example, when taking a full mouth series, contacts on the holder and receptor 30 can be used to identify which type of image is being taken. To identify if the upper or lower teeth are being imaged, a gravity sensor, for example as described in U.S. Pat. No. 7,775,713, incorporated by reference herein, could be used with the receptor 30 or the holder (see FIGS. 15A and 15B). As illustrated in FIGS. 15A and 15B, a receptor 30 can be connected to a holder 270 and can be used in a first position (see FIG. 15A) when taking images of upper teeth and can be used in a position (see FIG. 15B) when taking images of lower teeth. The receptor 30 can include a gravity sensor 275 that is used to detect a gravity value ("GV") to determine whether the holder 270 and the receptor 30 is positioned in the first position or the second position. As illustrated in FIGS. 15A and 15B, when a gravity sensor 275 is used, the receptor 30 can be keyed in the holder 270 (e.g., shaped to fit in only one orientation) or otherwise coupled to the holder in a consistent and precise manner to ensure that the receptor 30 is in the same position relative to the holder 270 every time it is used.

Figure 16A:
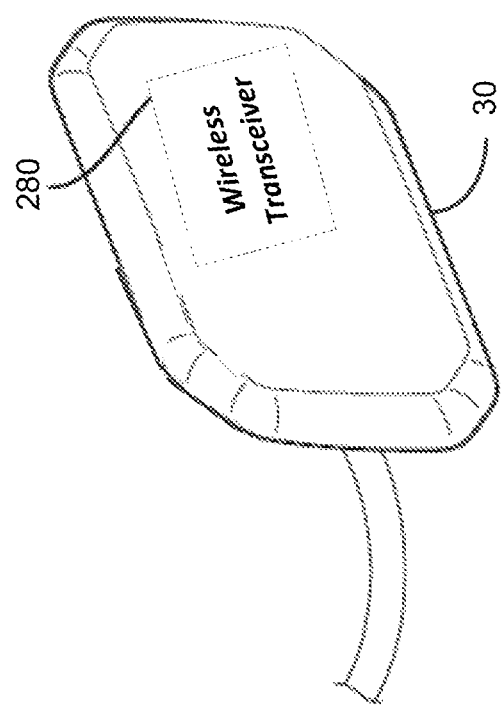
FIG. 16A illustrates a receptor used in the x-ray system of FIG. 1A or 2, the receptor including a wireless transceiver.
Figure 16B:
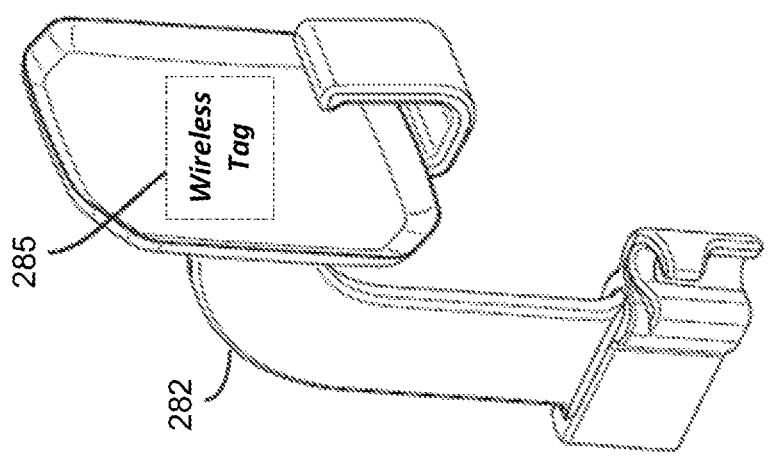
FIG. 16B illustrates a receptor holder used in the x-ray system of FIG. 1A or 2, the holder including a wireless tag detectable by the wireless transceiver included in the receptor of FIG. 16A.

In addition or alternatively, as illustrated in FIGS. 16A and 16B, a receptor 30 can include one or more wireless transceivers 280, including for example, a radio-frequency identification ("RFID") transceiver, a near-field communication ("NFC") transceiver, or other wireless transceivers, and a receptor holder 282 can include one or more wireless tags 285, including for example, a RFID tag, a NFC tag, or other wireless tags. Alternatively, or in addition, the wireless transceiver(s) 280 can be in the holder 282 and the wireless tag(s) 285 can be in the receptor 30, or both the receptor 30 and holder 282 can have one or more transceivers 280 and one or more tags 285. Furthermore, the wireless tag 285 can be either active (e.g., battery-powered) or passive. A wireless tag 285 on the receptor holder 282 can, for example, identify the kind of holder.

A wireless tag 285 can, but need not be, connected to a power source (e.g., the image processing unit 40) through a wire or cable, since it can also receive power wirelessly from the incoming electromagnetic (e.g., RF) signal. For example, a wireless tag 285 on the receptor holder can use the electromagnetic power that it receives from the transceiver 280 in the receptor 30 to charge a battery and/or power a microcontroller or other logic circuitry on or within the holder, in a manner similar to that used in the wireless identification and sensing platform ("WISP") technology. The logic circuitry can, for example, be connected to the contacts 212, optical sensors, magnetic sensors, gravity sensors, and/or other sensors on the receptor holder. By detecting the arrangement of electrical connections between the holder and the receptor, and/or by receiving signals from the various sensors in or on the receptor holder, the logic circuitry in/on the holder can determine the orientation of the receptor with respect to the holder and/or the orientation of the patient 31 and can transmit the orientation information back to the transceiver 280 in the receptor. The receptor 30 can then send the orientation information back to the image processing unit 40.

In addition, although the examples above use a cable 32 connected to the receptor 30 to transmit the image characteristic information to the image processing unit 40, the cable 32 can also be connected and transmit the image characteristic information: (1) from the receptor 30 to the x-ray controller 18, (2) from the receptor holder to the image processing unit 40, and/or (3) from the receptor holder to the x-ray controller 18.

Figure 17:
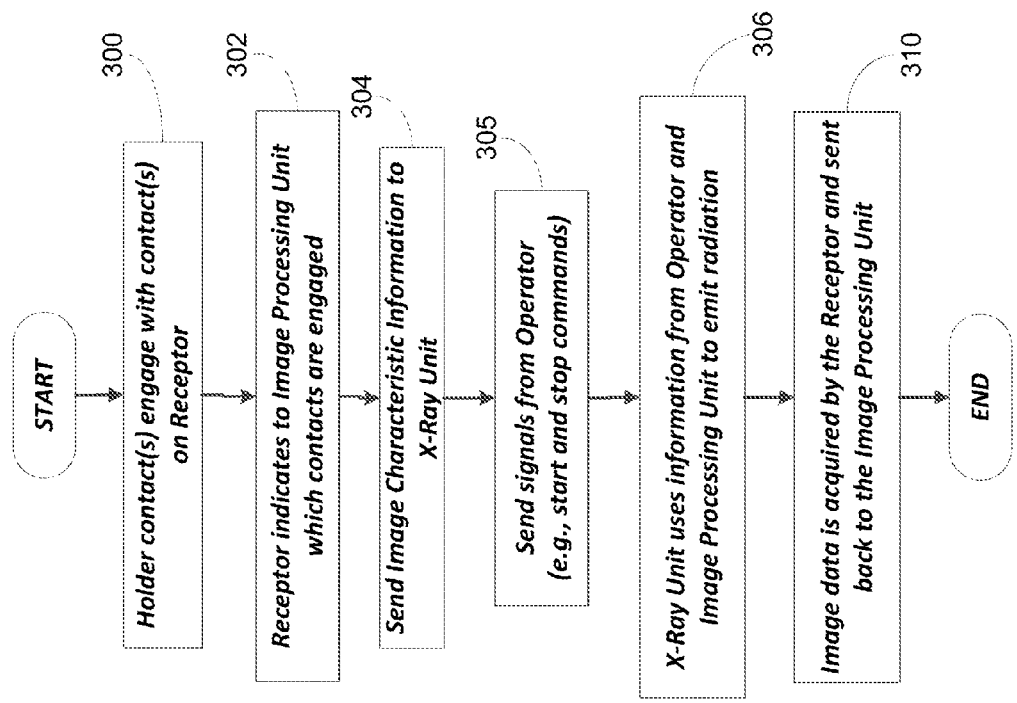
FIG. 17 is a flow chart illustrating another alternative method of automatically adjusting exposure parameters using receptor holders used in the x-ray system of FIG. 1A or 2.

FIG. 17 is a flowchart illustrating a method of automatically adjusting exposure parameters using the holders to identify a type of image being taken. As illustrated in FIG. 17, the receptor 30 is positioned in the holder such that the holder's contacts engage with contacts on the receptor 30 (at 300). The receptor 30 is configured to sense the engagements of one or more of the contacts and provide this information to the image processing unit 40 (at 302). The image processing unit 40 uses the information about the contacts to identify the type of holder being used and, consequently, the type of image being taken. The image processing unit 40 then sends image characteristic information to the x-ray unit based on the identified image type (at 304). As noted above, the image characteristic information can include exposure parameters or an identifier of a particular image type or image sequence.

Upon receiving the image characteristic information, the controller 18 controls the x-ray source 12 based on the image characteristic information provided by the image processing unit 40 and any signals or commands received from the operator (e.g., start and stop commands from a remote switch) (at 305) to emit appropriate radiation (at 306). The receptor 30 then acquires image data and forwards the image data to the image processing unit 40 (at 310). The image processing unit 40 can process the image data to generate an image and, optionally, display the generated image on a display device 43. It should be understood that in some embodiments, the receptor 30 can communicate image characteristic information (e.g., based on the electrical contacts) directly to the controller 18 rather than through the image processing unit 40. In addition, the information provided by the receptor 30 regarding the contacts can also be used (e.g., by the image processing unit 40 and/or the controller 18) to map acquired images to a proper location within a tooth map (see, e.g., FIG. 4) or otherwise store metadata with the acquired image regarding the type of the image. Accordingly, the automatic detection of the image type through the use of the electrical contacts allows the image processing unit 40 and/or the controller 18 to automatically categorize an image, which results in improved data management and overall patient service. Similarly, the image processing unit 40 and/or the controller 18 can be configured to generate a warning if the holder and an image selected by the operator do not match. For example, if the operator requests acquisition of a bitewing image but the receptor 30 detects engagement of electrical contacts associated with an endodontic holder, the image processing unit 40 and/or the controller 18 can generate a visual or audible warning to the operator.

Thus, the invention provides, among other things, systems and methods for automatically setting exposure parameters for images acquired with an intraoral imaging system. Automatically adjusting the exposure settings results in minimized radiation exposure for the patient, image quality, and eliminates the possibility of manual errors. In some embodiments, the systems and methods can automatically identify a current image being taken using electrical contacts on the x-ray receptor and mating contacts on the holder for the receptor. It should be understood that the systems and methods disclosed herein can be used in other types of imaging systems and is not limited to intra-oral dental imaging. Furthermore, it should be understood that the data tables described above can be stored and constructed in various formats and with more or fewer exposure parameters or other parameters than as illustrated herein. Also, in some embodiments, the data tables can be replaced or used in combination with algorithms that define the parameters for particular types of images. In addition, it should be understood that the functionality performed by the image processing unit 40 and the controller 18 can be combined and distributed in numerous configurations.

Various features and advantages of the invention are set forth in the following claims.

What is claimed is:
1. An x-ray system comprising:
an x-ray source having at least one adjustable exposure parameter, and
at least one controller having memory storing a plurality of image types and a plurality of predetermined settings of the at least one adjustable exposure parameter, the at least one controller configured to associate each of the plurality of image types with one of the plurality of predetermined settings, the at least one controller further configured to automatically select an image type based on image characteristic information, the image characteristic information including an identifier of a type of an x-ray receptor holder, the at least one controller further configured to select one of the plurality of predetermined settings based on the selected image type, the at least one controller further configured to adjust the at least one adjustable exposure parameter based on the selected one of the plurality of predetermined settings.

2. The x-ray system as claimed in claim 1, wherein the image characteristic information further includes an identifier of a predefined sequence of images.

3. The x-ray system as claimed in claim 2, wherein the at least one controller is configured to automatically identify a set of values of the at least one adjustable exposure parameter for each image included in the predefined sequence of images.

4. The x-ray system as claimed in claim 2, wherein the at least one controller is configured to automatically identify, based on the identifier of the predetermined sequence of images, a first set of values of the at least one adjustable exposure parameter for a first sub-set of images included in the predefined sequence of images and a second set of values of the at least one adjustable exposure parameter for a second sub-set of images included in the predefined sequence of images.

5. The x-ray system as claimed in claim 4, wherein the at least one controller is configured to automatically identify the first set of values and the second set of values by accessing at least one data table associated with the predefined sequence of images.

6. The x-ray system as claimed in claim 4, wherein the at least one controller is configured to cause the x-ray source to operate based on the first set of values of the at least one adjustable exposure parameter to generate the first sub-set of images and operate based on the second set of values of the at least one adjustable exposure parameter to generate the second sub-set of images.

7. The x-ray system as claimed in claim 1, wherein the image characteristic information further includes image type information, and wherein the at least one controller is configured to automatically identify a set of values of the at least one adjustable exposure parameter based on the image type information.

8. The x-ray system as claimed in claim 7, wherein the at least one controller is configured to automatically identify the set of values by accessing at least one data table.

9. The x-ray system as claimed in claim 1, wherein the image characteristic information further includes a set of values of the at least one adjustable exposure parameter.

10. The x-ray system as claimed in claim 1, wherein the at least one controller is configured to adjust at least one of the plurality of predetermined settings based on a measured exposure level of a previous image.

11. The x-ray system as claimed in claim 1, wherein the at least one controller is configured to automatically identify the set of values by accessing a data table.

12. The x-ray system as claimed in claim 1, wherein the at least one controller comprises a first controller and a second controller, and wherein the first controller is configured to receive the image characteristic information from the second controller.

13. The x-ray system as claimed in claim 12, wherein the second controller generates the image characteristic information based on input from an operator.

14. The x-ray system as claimed in claim 13, wherein the input from the operator indicates an operator selection of at least one of a predefined sequence of images and an image type.

15. The x-ray system as claimed in claim 1, wherein the image characteristic information further includes image type information and further comprising an x-ray receptor and an x-ray receptor holder, the x-ray receptor holder having at least one indicator element configured to indicate the image type information, the x-ray receptor having at least one detector configured to detect the at least one indicator element.

16. The x-ray system as claimed in claim 15, wherein the at least one indicator element comprises an electrical contact.

17. The x-ray system as claimed in claim 15, wherein the at least one indicator element comprises an optical pattern.

18. The x-ray system as claimed in claim 15, wherein the at least one indicator element comprises at least one selected from the group consisting of magnet and a magnetic pattern.

19. The x-ray system as claimed in claim 1, further comprising a plurality of x-ray receptor holders, each holder having a unique arrangement of contacts configured to engage contacts of an x-ray receptor, and wherein a signal is generated based on engagement between the contacts of the holder and the contacts of the x-ray receptor, wherein the at least one controller receives the signal as the image characteristic information.

20. An x-ray system comprising:
a first controller; and
at least one x-ray receptor holder, the at least one x-ray receptor holder having at least one contact configured to engage at least one contact of an x-ray receptor, wherein the at least one contact of the at least one holder and the at least one contact of the receptor are arranged to produce a signal based on engagement between the at least one contact of the at least one holder and the at least one contact of the x-ray receptor, the signal indicating one of the group consisting of an orientation of the receptor and a receptor holder type,
wherein the first controller is configured to receive the signal and to control an x-ray source to operate based on the signal.

21. The x-ray system as claimed in claim 20, wherein the first controller is configured to determine image characteristic information based on the signal, and is further configured to control the x-ray source to operate based on the signal by sending the image characteristic information to a second controller controlling the x-ray source.

22. The x-ray system as claimed in claim 20, wherein the first controller is configured to identify a set of values of at least one adjustable exposure parameter of the x-ray source based on the signal and is further configured to control the x-ray source to operate based on the set of values.

23. The x-ray system as claimed in claim 22, wherein the first controller is configured to automatically identify the set of values by accessing at least one data table.

24. A method of operating an x-ray system comprising an x-ray source and at least one controller, the at least one controller having a memory, the x-ray source having at least one adjustable exposure parameter, the method comprising:
storing, in the memory, a plurality of image types and a plurality of predetermined settings of the at least one adjustable exposure parameter;
associating each of the plurality of image types with one of the plurality of predetermined settings;
automatically selecting, by the at least one controller, an image type based on image characteristic information, the image characteristic information comprising an identifier of a type of an x-ray receptor holder;
selecting, by the at least one controller, one of the plurality of predetermined settings based on the selected image type; and
adjusting, by the at least one controller, the at least one adjustable exposure parameter based on the selected one of the plurality of predetermined settings.

25. The method as claimed in claim 24, further comprising identifying, based on image sequence information, a first value of the at least one adjustable exposure parameter for a first sub-set of images included in a predefined sequence of images associated with the image sequence information and a second value of the at least one adjustable exposure parameter for a second sub-set of images included in the predefined sequence of images based on at least one data table associated with the image sequence information.

26. The method as claimed in claim 25, further comprising receiving the image sequence information at a second controller.

27. The method as claimed in claim 26, further comprising transmitting the image characteristic information based on the image sequence information from the second controller to the at least one controller.

28. The method as claimed in claim 24, further comprising adjusting, by the at least one controller, the at least one adjustable exposure parameter based on an exposure level of a previous image.

29. A method of operating an x-ray system comprising an x-ray source and at least one controller, the at least one controller having a memory, the x-ray source having at least one adjustable exposure parameter, the method comprising:
 storing, in the memory, a plurality of image types and a plurality of predetermined settings of the at least one adjustable exposure parameter;
 associating each of the plurality of image types with one of the plurality of predetermined settings;
 automatically selecting, by the at least one controller, an image type based on image characteristic information, the image characteristic information comprising an identifier of a predefined sequence of images;
 selecting, by the at least one controller, one of the plurality of predetermined settings based on the selected image type; and
 adjusting, by the at least one controller, the at least one adjustable exposure parameter based on the selected one of the plurality of predetermined settings,
 wherein adjusting the at least one adjustable exposure parameter includes automatically identifying, based on the identifier of the predefined sequence of images, a first set of values of the at least one adjustable exposure parameter for a first sub-set of images included in the predefined sequence of images and a second set of values of the at least one adjustable exposure parameter for a second sub-set of images included in the predefined sequence of images.

30. The method as claimed in claim 29, further comprising automatically identifying a set of values of the at least one adjustable exposure parameter for each image included in the predefined sequence of images.

31. The method as claimed in claim 29, further comprising image type information, and automatically identifying a set of values of the at least one adjustable exposure parameter based on the image type information.

32. The method as claimed in claim 31, wherein automatically identifying the set of values of the at least one adjustable exposure parameter includes accessing at least one data table.

33. The method as claimed in claim 29, further comprising a set of values of the at least one adjustable exposure parameter.

* * * * *